(12) United States Patent
Kassegne et al.

(10) Patent No.: US 10,758,136 B2
(45) Date of Patent: Sep. 1, 2020

(54) HYBRID METAL AND CARBON OR GLASSY CARBON MEMS μ-ECOG ELECTRODE AND MICROELECTRODE STRUCTURES

(71) Applicant: San Diego State University Research Foundation (SDSURF), San Diego, CA (US)

(72) Inventors: Samuel Kassegne, Carlsbad, CA (US); Pieter van Niekerk, Murrieta, CA (US); Maria Vomero, San Diego, CA (US)

(73) Assignee: San Diego State University (SDSU) Research Foundation, San Diego, CA (US)

( * ) Notice: Subject to any disclaimer, the term of this patent is extended or adjusted under 35 U.S.C. 154(b) by 328 days.

(21) Appl. No.: 14/855,738

(22) Filed: Sep. 16, 2015

(65) Prior Publication Data

US 2016/0073920 A1 Mar. 17, 2016

Related U.S. Application Data

(60) Provisional application No. 62/093,787, filed on Dec. 18, 2014, provisional application No. 62/051,295, filed on Sep. 16, 2014.

(51) Int. Cl.
*A61B 5/0478* (2006.01)
*A61B 5/0492* (2006.01)
(Continued)

(52) U.S. Cl.
CPC ........ *A61B 5/04001* (2013.01); *A61B 5/0478* (2013.01); *A61B 5/0492* (2013.01);
(Continued)

(58) Field of Classification Search
CPC .................................................. A61B 5/04001
(Continued)

(56) References Cited

U.S. PATENT DOCUMENTS

| 4,461,304 A | * | 7/1984 | Kuperstein | ........ A61B 5/04001 |
| | | | | 439/70 |
| 4,773,433 A | * | 9/1988 | Richter | ................ A61N 1/0565 |
| | | | | 607/119 |

(Continued)

OTHER PUBLICATIONS

Evolution of Glassy Carbon Microstructure: In Situ Transmission Electron Microscopy of the Pyrolysis Process Swati Sharma, C. N. Shyam Kumar, Jan G. Korvink & Christian Kübel Scientific Reports vol. 8, Article No. 16282 (2018).
(Continued)

*Primary Examiner* — Lee S Cohen
(74) *Attorney, Agent, or Firm* — Sandra Poteat Thompson; Finlayson Toffer Roosevelt & Lilly LLP

(57) ABSTRACT

Microelectromechanical system are disclosed that include at least one electrode, microelectrode or combination thereof, wherein the at least one electrode comprises a carbon material, a glassy carbon material or a combination thereof. Contemplated systems are suitable for μ-ECoG arrays. Additional microelectromechanical systems are disclosed that include at least one electrode, microelectrode or combination thereof, wherein the at least one electrode comprises a carbon material, a glassy carbon material or a combination thereof; at least one substrate, surface, layer or a combination thereof, wherein the at least one electrode, microelectrode or combination thereof is disposed on, coupled with or otherwise layered on the at least one substrate, surface, layer or a combination thereof; and at least one bump pad, wherein the at least one electrode, microelectrode or combination thereof is coupled with the at least one bump pad via at least one conductive metal. A method of making a
(Continued)

Fabrication procedure for metal-CMEMS glassy carbon electrode microelectromechanical system includes patterning a polymer precursor, a carbon-containing material or a combination thereof onto a surface, a substrate, at least one layer or a combination thereof; and heating or pyrolysing the polymer precursor, a carbon-containing material or a combination thereof in order to form a glassy carbon material. Uses of microelectromechanical systems are also contemplated to measure at least one electrical property in a mammal or for electrocorticography.

12 Claims, 16 Drawing Sheets

(51) Int. Cl.
    *A61B 5/04*         (2006.01)
    *A61B 5/00*         (2006.01)
    *G03F 7/40*         (2006.01)
    *G03F 7/038*       (2006.01)

(52) U.S. Cl.
    CPC ............ *A61B 5/4836* (2013.01); *G03F 7/038* (2013.01); *G03F 7/40* (2013.01)

(58) Field of Classification Search
    USPC ................................................ 600/377, 378
    See application file for complete search history.

(56) References Cited

U.S. PATENT DOCUMENTS

| | | | | |
|---|---|---|---|---|
| 6,834,200 | B2* | 12/2004 | Moxon | A61B 5/04001 600/373 |
| 7,079,903 | B2* | 7/2006 | O'Brien | A61N 1/05 600/374 |
| 8,738,110 | B2* | 5/2014 | Tabada | A61N 1/05 600/378 |
| 2007/0016268 | A1 | 1/2007 | Carter | A61N 1/05 607/69 |
| 2007/0239059 | A1* | 10/2007 | McIver | A61B 5/04009 600/544 |
| 2008/0249391 | A1* | 10/2008 | Moxon | A61B 5/04001 600/373 |
| 2012/0186998 | A1* | 7/2012 | Hermans | A61B 5/1486 205/780.5 |
| 2013/0079615 | A1* | 3/2013 | Yoon | A61B 5/04001 600/377 |
| 2015/0369771 | A1* | 12/2015 | Richardson-Burns | A61B 5/0408 600/372 |
| 2016/0007874 | A1* | 1/2016 | Ma | A61B 5/04001 600/374 |
| 2017/0238832 | A1* | 8/2017 | Tcheng | A61B 5/0478 |

OTHER PUBLICATIONS

Nimbalkar, S., Castagnola, E., Balasubramani, A., Scarpellini, A., Samejima, S., Khorasani, A., Boissenin, A., Thongpang, S., Moritz, C., and Kassegne, S., "Ultra-Capacitive Carbon Neural Probe Allows Simultaneous Long-Term Electrical Stimulations and High-Resolution Neurotransmitter Detection", Nature Scientific Reports 8 (1), 6958, 2018.

Hirabayashi, M., Logan, K., Deutschman, CP., McDowell, TW., Torres, M., Pullman, D., Kassegne, S., "Investigation of Interface Bonding Mechanisms between Glassy Carbon Microelectrodes and Polyimide Substrate through Fourier Transform Infrared Spectroscopy", Journal of the Electrochemical Society 165 (8), B3060-B3070, 2018.

Castagnola, E., Vahidi, N., Nimbalkar, S., Rudraraju, S., Thielk, M., Zucchini, E., Cea, C., Carli, S., Gentner, T., Ricci, D., Fadiga, L., Kassegne, S., "In Vivo Dopamine Detection and Single Unit Recordings Using Intracortical Glassy Carbon Microelectrode Arrays", MRS Advances, 1-6, 2018.

Vomero, M., Castagnola, E., Ciarpella, F., Maggiolini, E., Goshi, N., Zucchini, E., Carli, S., Fadiga, L., Kassegne, S., Ricci, D., "Highly Stable Glassy Carbon Interfaces for Long-Term Neural Stimulation and Low-Noise Recording of Brain Activity", Nature Scientific Reports, vol. 7, 4033, DOI: 10.1038/srep40332, 2017.

Hirabayashi, M., Mehta, B, Vahidi, N, Khosla, A., and Kassegne, S., "Functionalization and Characterization of Pyrolyzed Polymer Based Carbon Microstructures for Bionanoelectronics Platform", JMM (Journal of Micromechanics and Microengineering), 23 (11), 115001, 2013.

Goshi, N., Castagnola, E., Vomero, C Gueli, C Cea, E Zucchini, D Bjanes, Maggiolini, E., Moritz, C., Kassegne, S., Ricci, D., Fadiga, L., "Glassy Carbon MEMS for Novel Origami-styled 3D Integrated Intracortical and Epicortical Neural Probes", Journal of Micromechanics and Microengineering 28 (6), 065009, 2018.

Huynh, N.U., Kassegne, S. & Youssef, G. Comparative study of tuning of microfabrication parameters for improving electrochemical performance of platinum and glassy carbon microelectrodes in neural prosthetics. Microsyst Technol 26, 775-785 (2020). https://doi.org/10.1007/s00542-019-04618-6.

\* cited by examiner

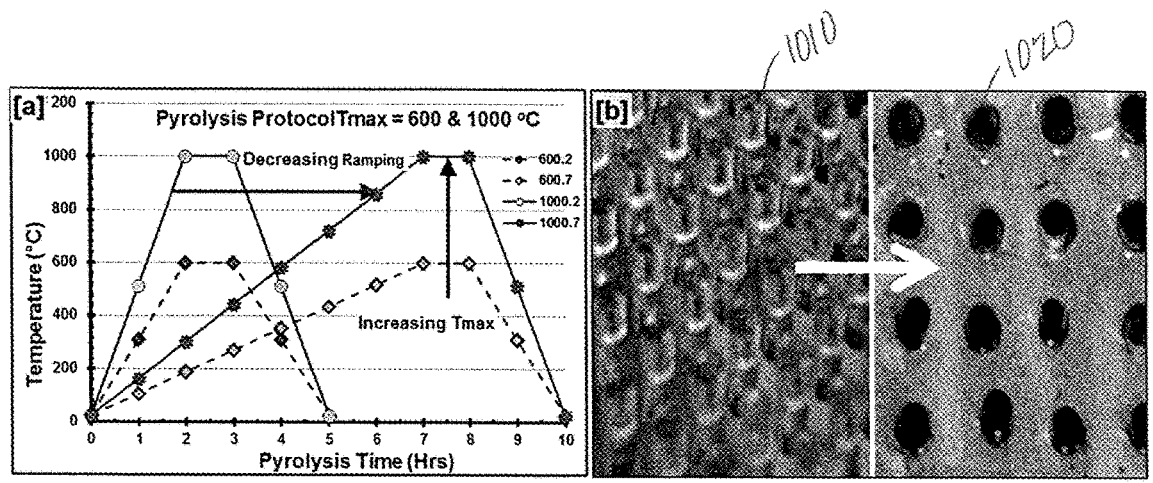

Figure 1. (a) Protocol for differing maximum pyrolysis temperatures and pyrolysis durations. For example, '600.2' and '1000.7' correspond to ramping rates of 4.8°C/min and 2.32°C/min respectively (b) negative photoresist (SU-8) is pyrolysed to glassy carbon pillars.

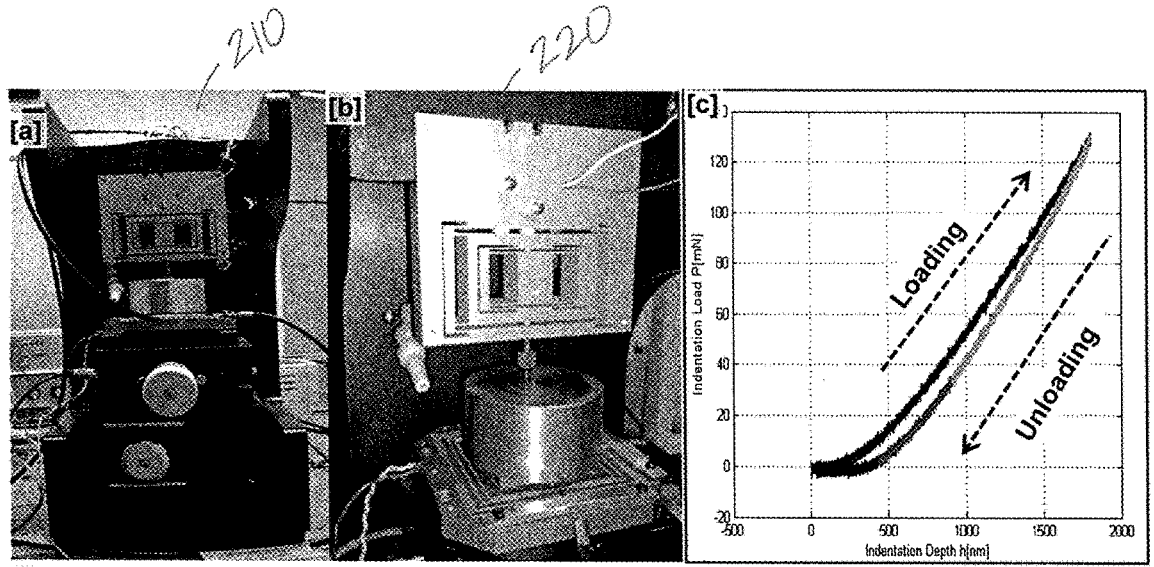

Figure 2. (a) Nano-indentation system for hardness and Young's Modulus test, (b) compliant z-stage with piezoelectric stack actuator, and (c) load-displacement curve.

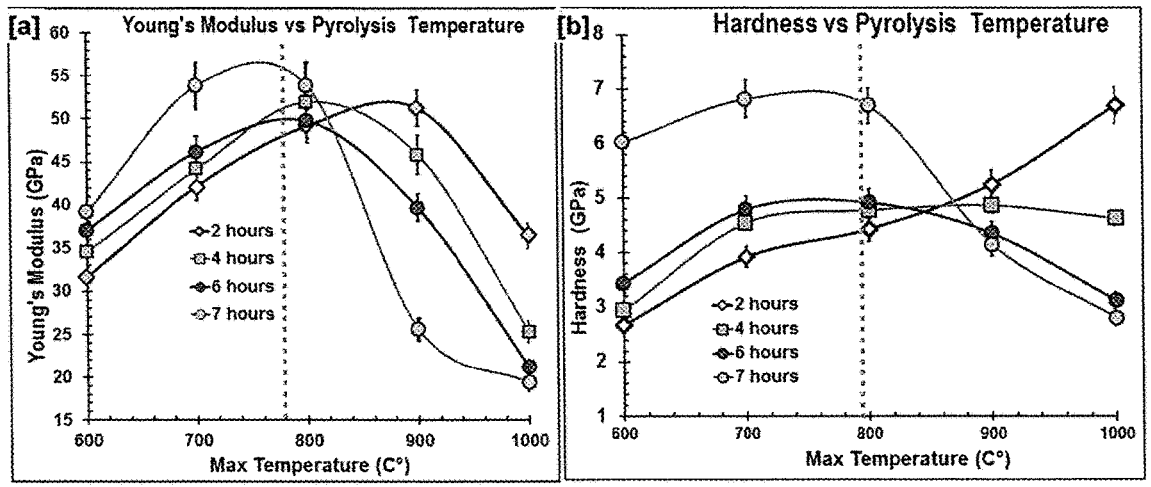
Figure 3. (a) Young's Modulus for a variety of pyrolysis temperatures, (b) hardness of electrodes for a variety of pyrolysis temperatures.
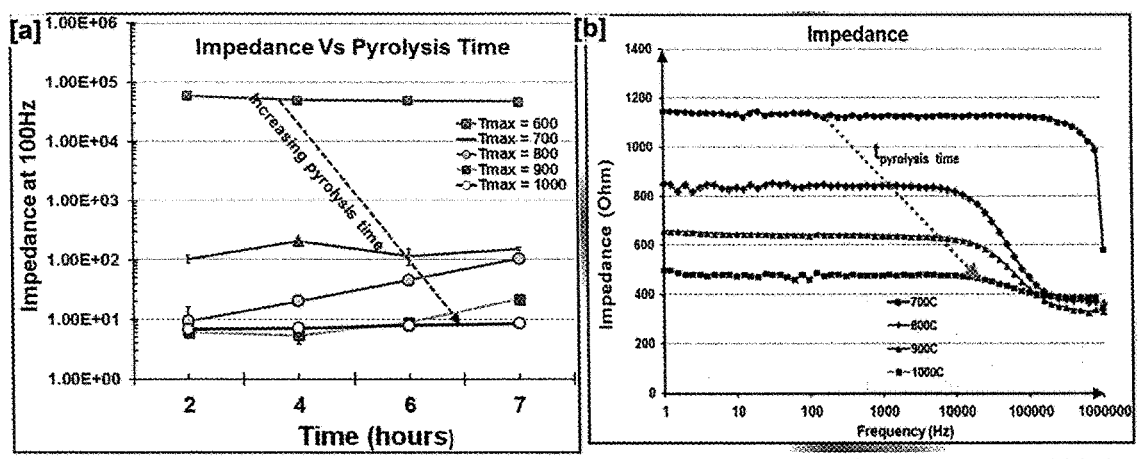
Figure 4. (a) Impedance for a variety of pyrolysis temperatures of electrodes at 100Hz, (b) Impedance vs frequency for a variety of pyrolysis temperatures for glassy carbon traces.

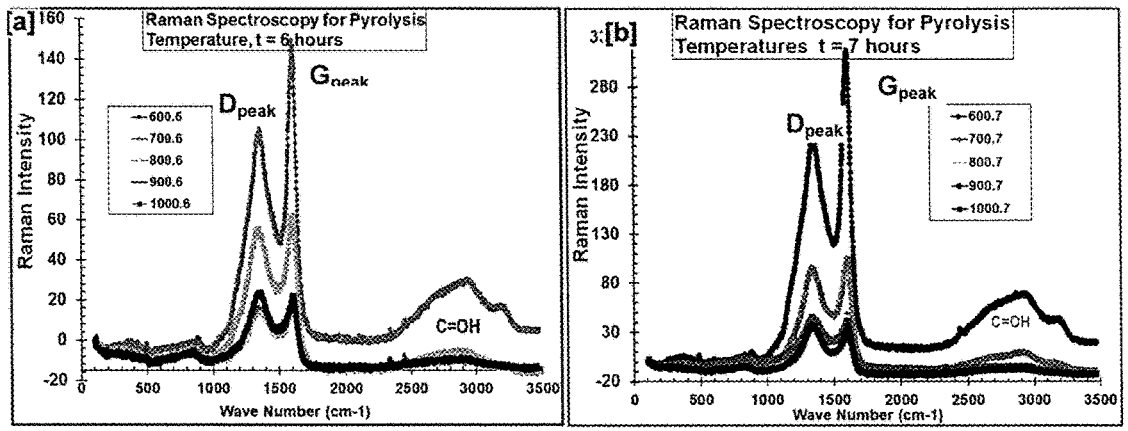
Figure 5. (a) Raman spectroscopy for a variety of pyrolysis temperatures at t=6 hours, (b) Raman spectroscopy for a variety of pyrolysis temperatures at t=7 hours
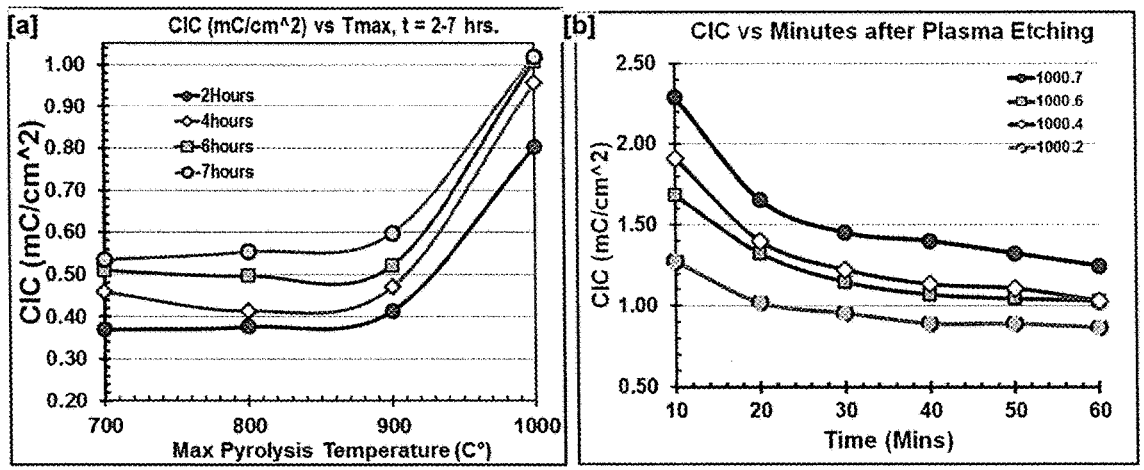
Figure 6. (a) CIC for a variety of pyrolysis temperatures, (b) Transient of CIC after plasma treatment for a variety of pyrolysis temperatures (100 Watts for 60 Sec). Shows a temporary effect.

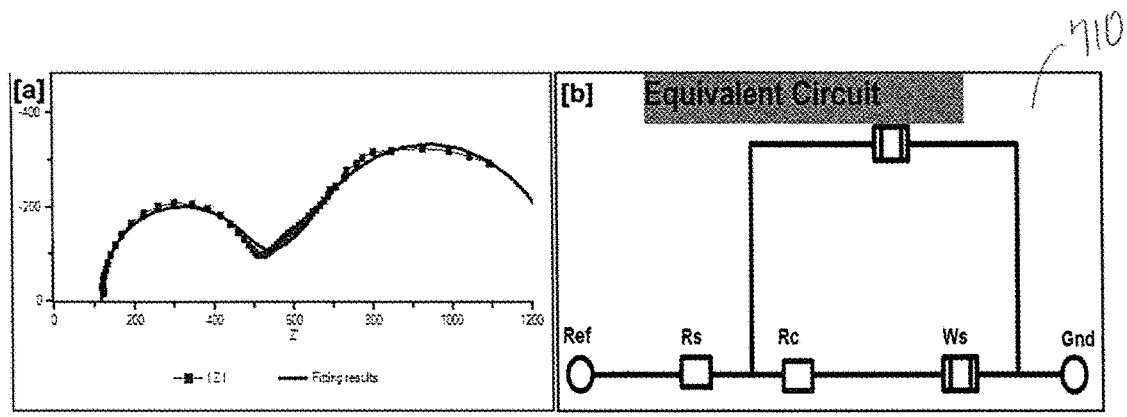

Figure 7. (a) Cyclic voltammetry measured and curve-fitting, (b) Equivalent Modified Randle circuit for the system. Rs = Solution Resistance, Rc = Charge Transfer Resistance (diameter of first semicircle), WS= Warburg Coefficient, CPE = Constant Phase Element at $\omega=1$.

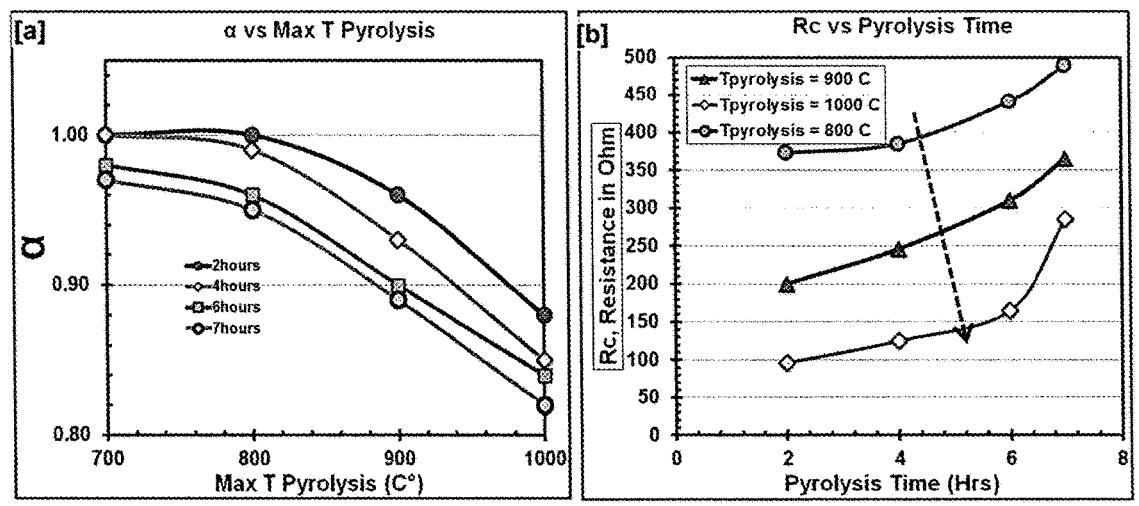

Figure 8. (a) Alpha (multiplication factor of phase angle) vs pyrolysis temperatures, (b) charge transfer resistance (Rc) vs time of pyrolysis.

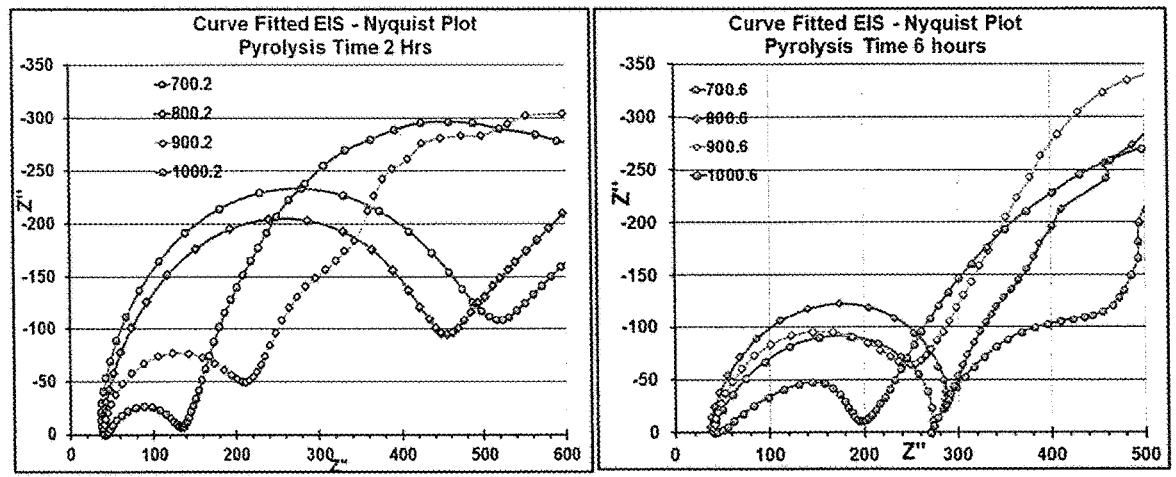
Figure 9. (a) Nyquist Plot for 6 hours of pyrolysis (b) Nyquist Plot for 7 hours of pyrolysis.
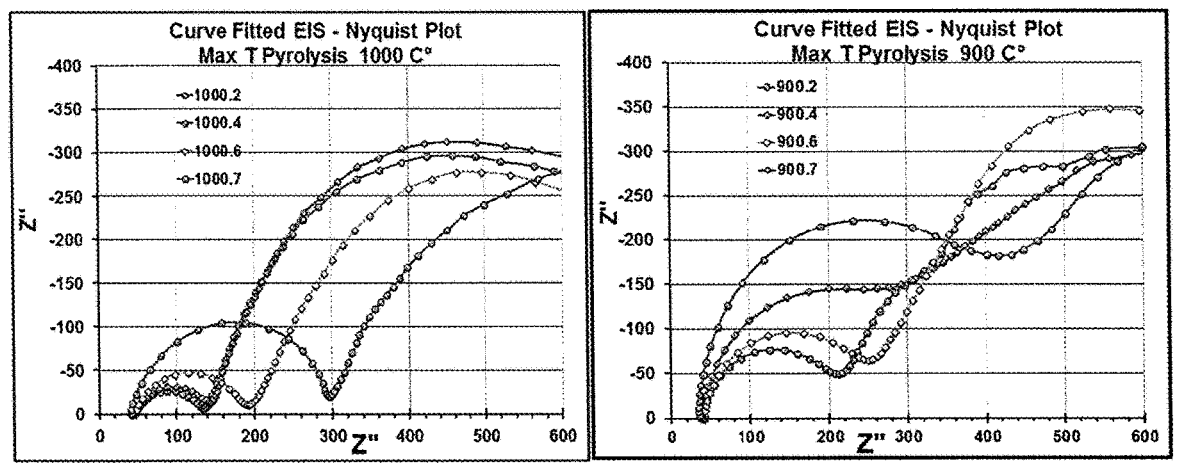
Figure 10. Fitted Nyquist Plots for 700-1000 °C pyrolysis temperature.

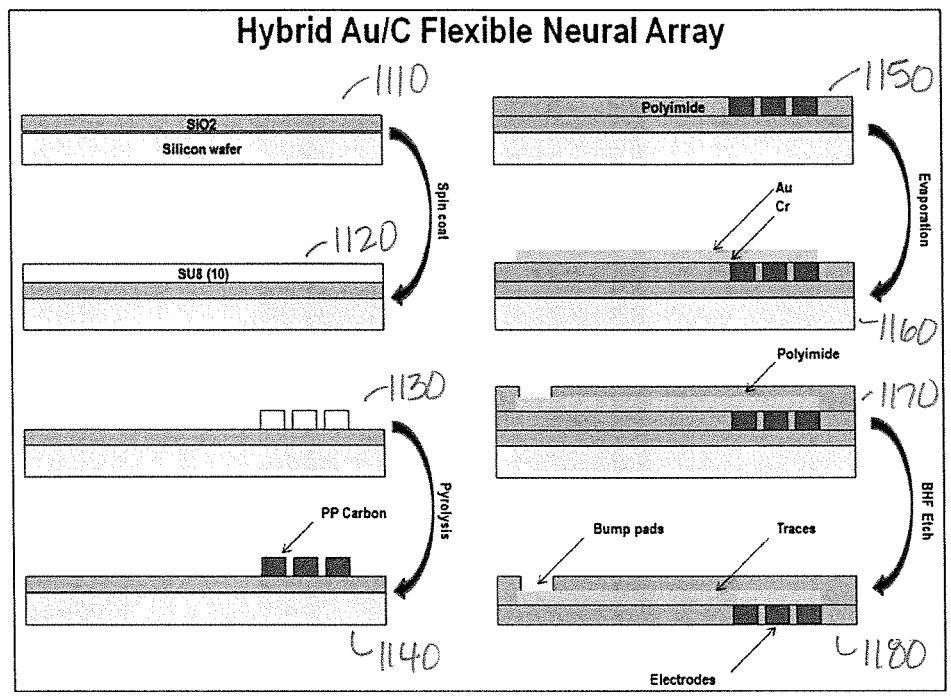
Figure 11. Fabrication procedure for metal-CMEMS glassy carbon electrode.

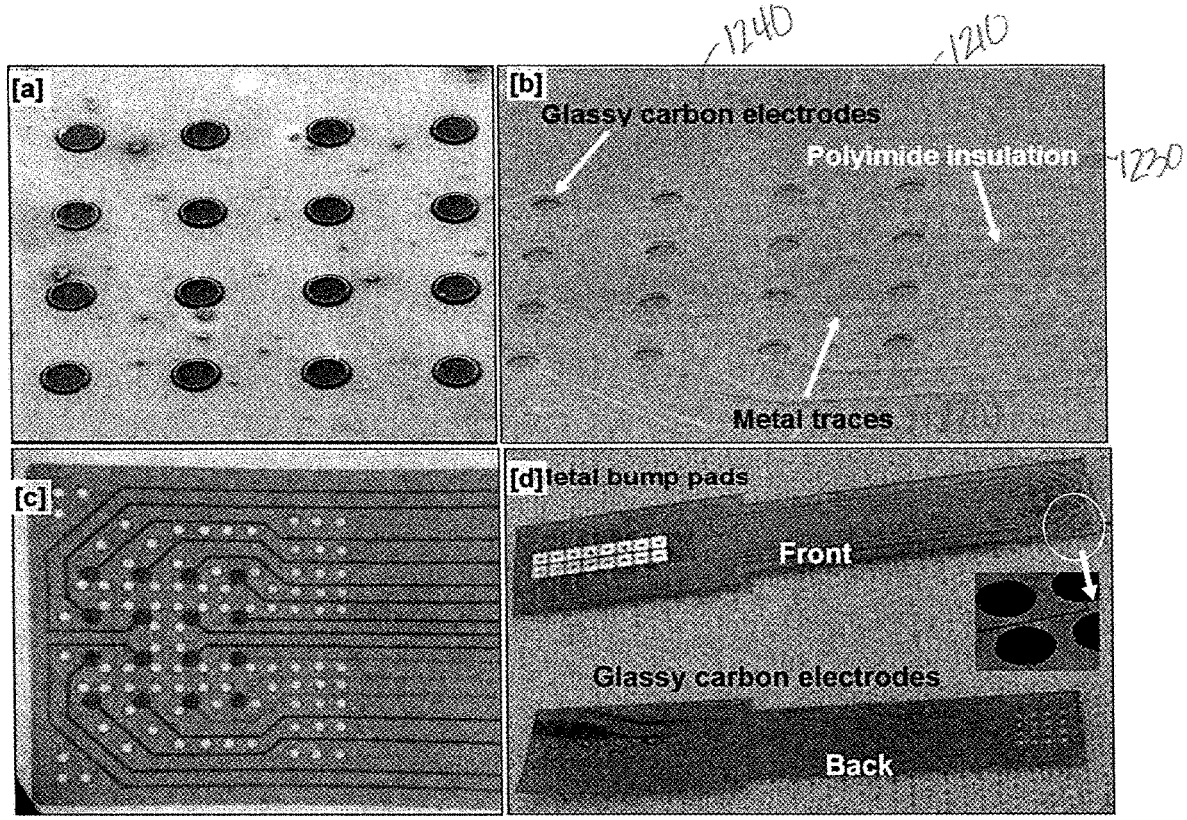

Figure 12. Hybrid metal and glassy electrode probes. (a) SEM of glassy carbon electrodes after pyrolysis, (b) SEM of GC-MEMS electrodes after pyrolysis and laying insulation layer, (c) bright-field microscope image of final microelectrode array, (d) front and back images of microelectrodes.

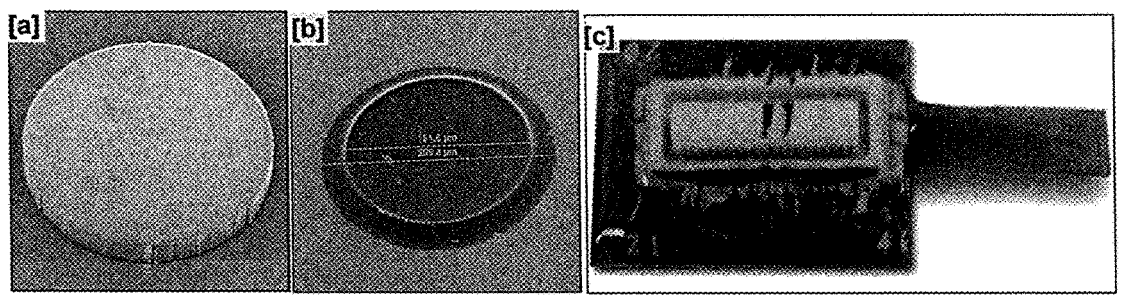

Figure 13. Details of a hybrid metal and glassy electrode probes. (a) SU-8 microelectrode before pyrolysis, (b) microelectrode structure after pyrolysis, (c) complete µECoG device with carbon electrodes connected to Hirose 40-pin connector, and glued to PCB for stability.

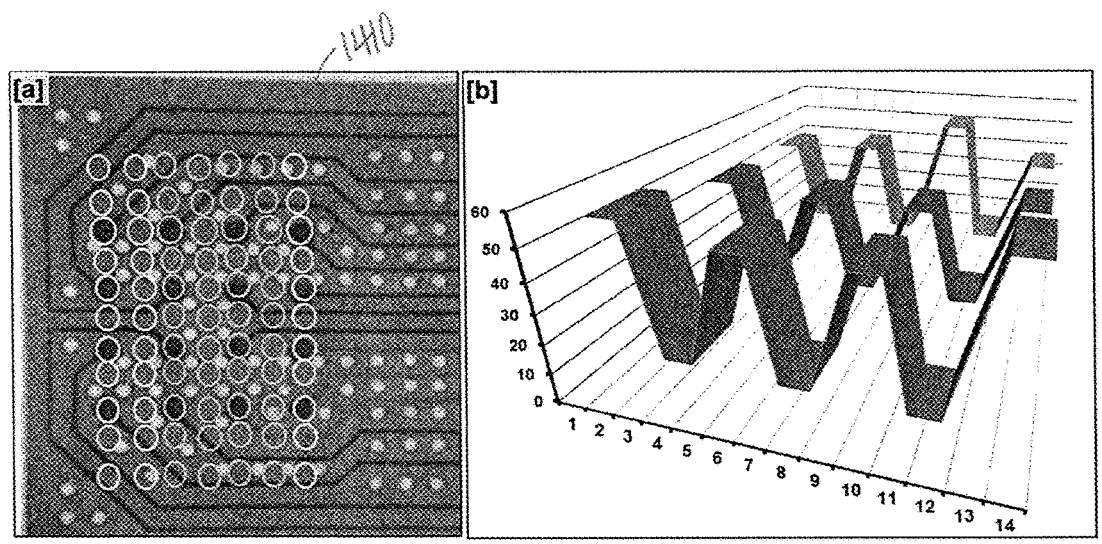
Figure 14. Mapping of Young's Modulus of Hybrid microelectrode array.
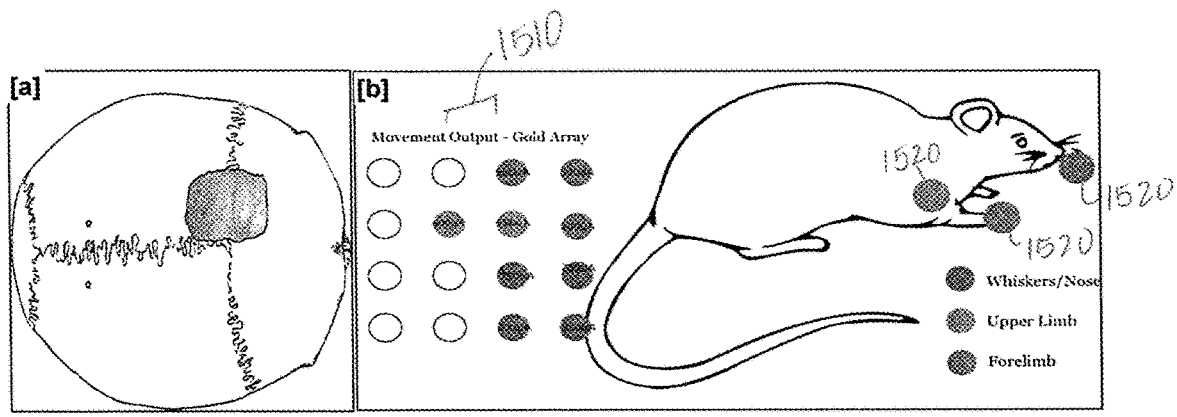
Figure 15. (a) Location of implantation of both Au/Pt and Au/C μECoG devices at motor cortex of rat model, (b) Electrode map and locations of elicited movements in anesthetized rat model.

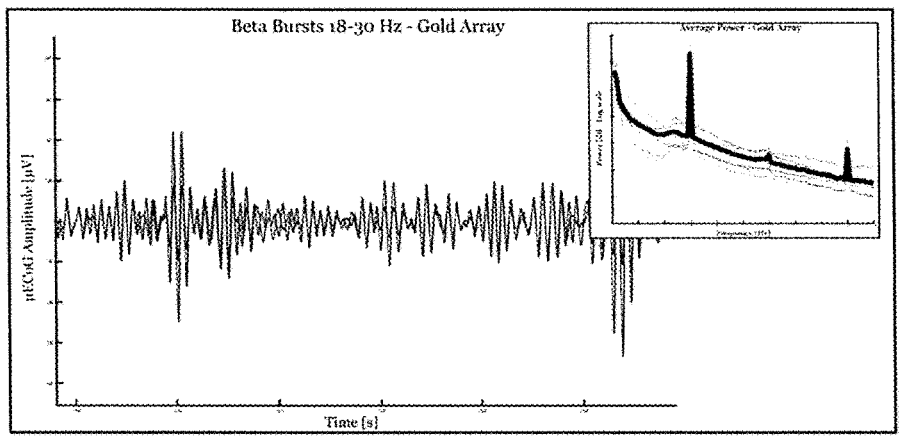
Figure 16. Beta activity (main) and power spectra (top right) recorded by gold μECoG on anesthetized rat.
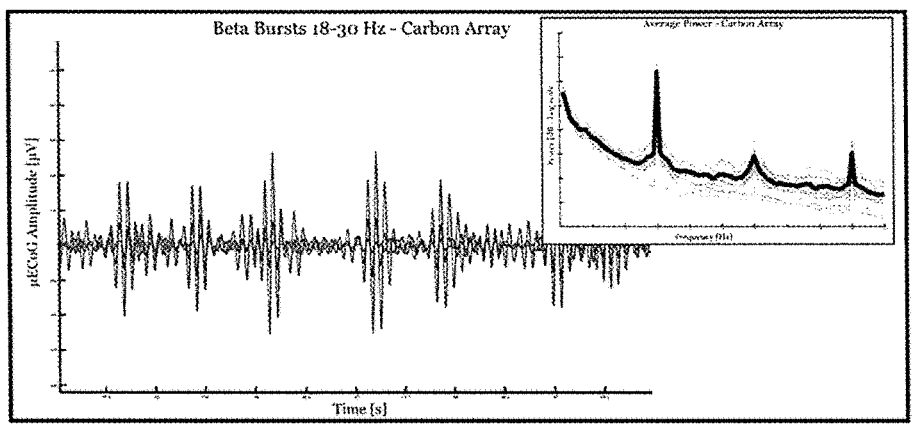
Figure 17. Beta activity (main) and power spectra (top right) recorded by carbon μECoG on anesthetized rat.

Figure 18: Lithography and pyrolysis process for fabricating glassy carbon electrodes from a negative tone photoresist. Silicon substrate with oxide layer is used. HF etches $SiO_2$ to release the final structure. The thickness of polyimide substrate is about 20 μm. Polyimide is cured at 375°C for 2 hours in $N_2$ atmosphere.

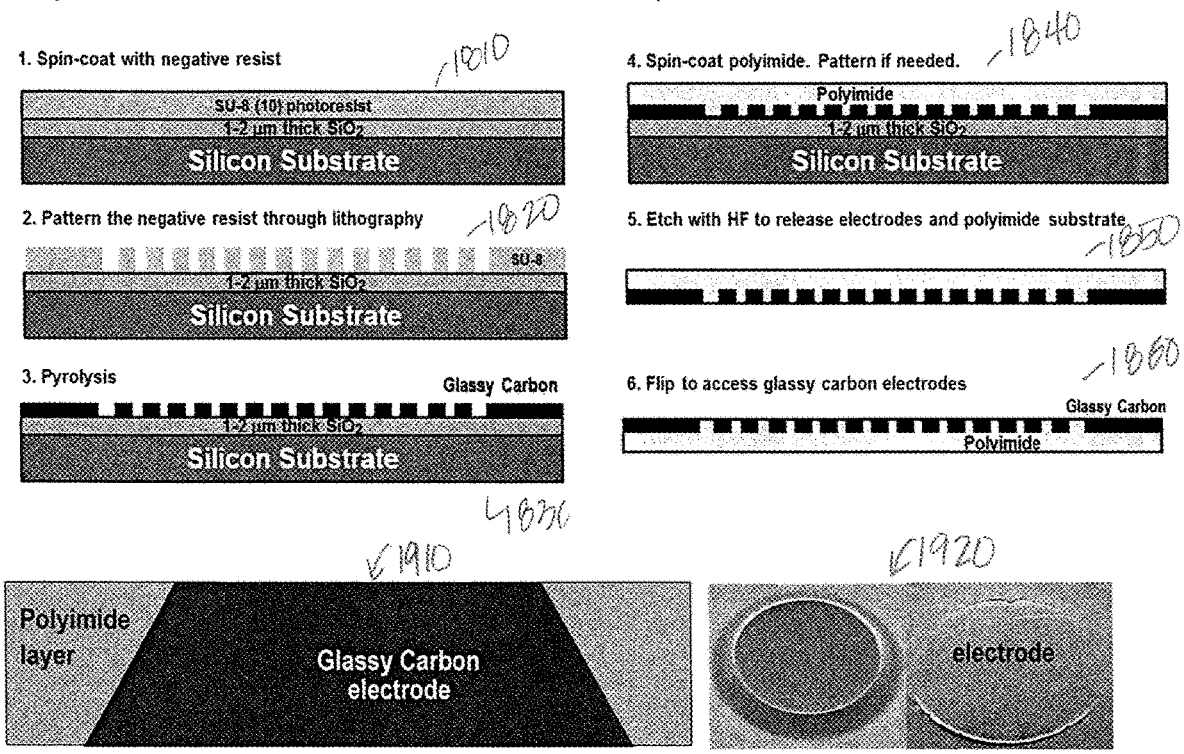

Figure 19 (a) Cross-section of pattern transfer process. (b) Shape of the pyrolysed electrodes is trapezoidal in elevation (conical in 3D) due to uneven shrinking during high-temperature pyrolysis process where both height and diameter decrease significantly. The bottom side that is constrained through attachment to silicon substrate shrinks less as compared to unconstrained sides. (c) electrodes flush with polyimide layer.

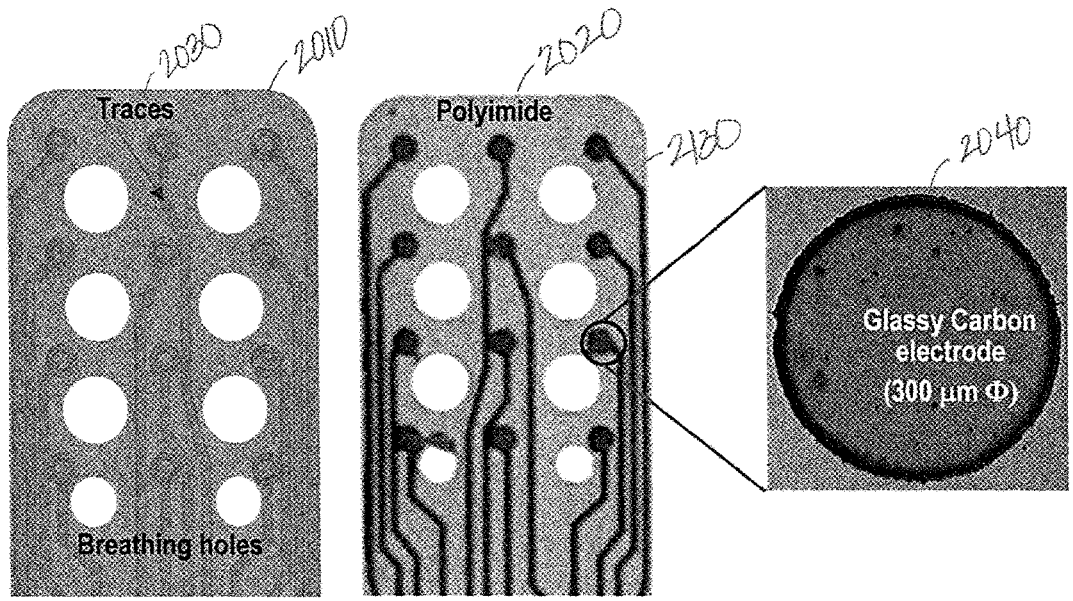

Figure 20. Complete glassy carbon electrode-set fabricated using the pattern transfer method described here. These microelectrode sets shown here (S1) are used for mechanical and electrical characterizations. The traces could be made from glassy carbon or metal [9]. The electrodes have a diameter of 300 μm whereas the traces are 90 μm wide.

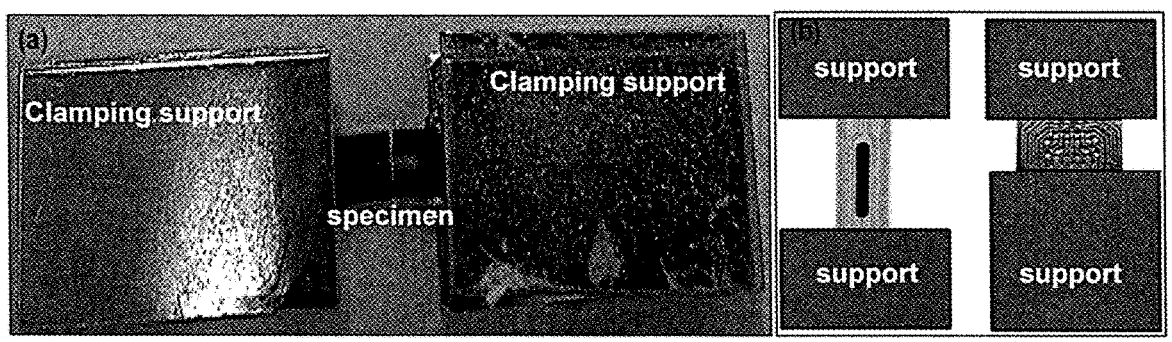

Figure 21 (a) Steel bracket sample holder with electrode set in preparation for tensile test, (b) location of clamp support for both geometries of probes tested. For S1, the area of interest is the upper middle part of the probe with traces and polyimide, whereas for S2, the area of interest comprises electrodes, traces and polyimide substrate.

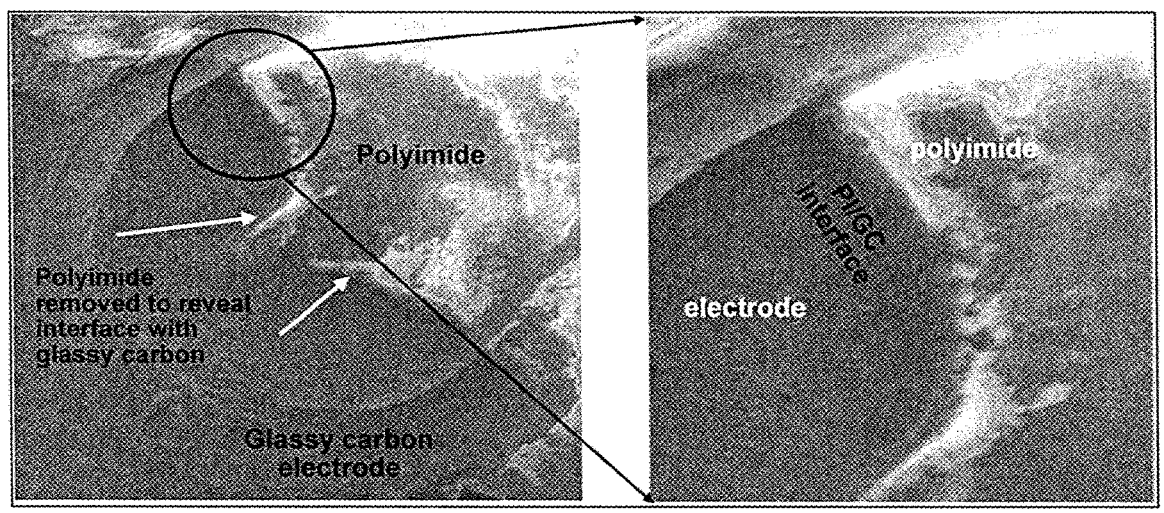
Figure 21c. Interface between polymer substrate and glassy carbon electrodes in S1 electrode set. In-set shows a close-up view of polyimide and glassy carbon electrode interface.

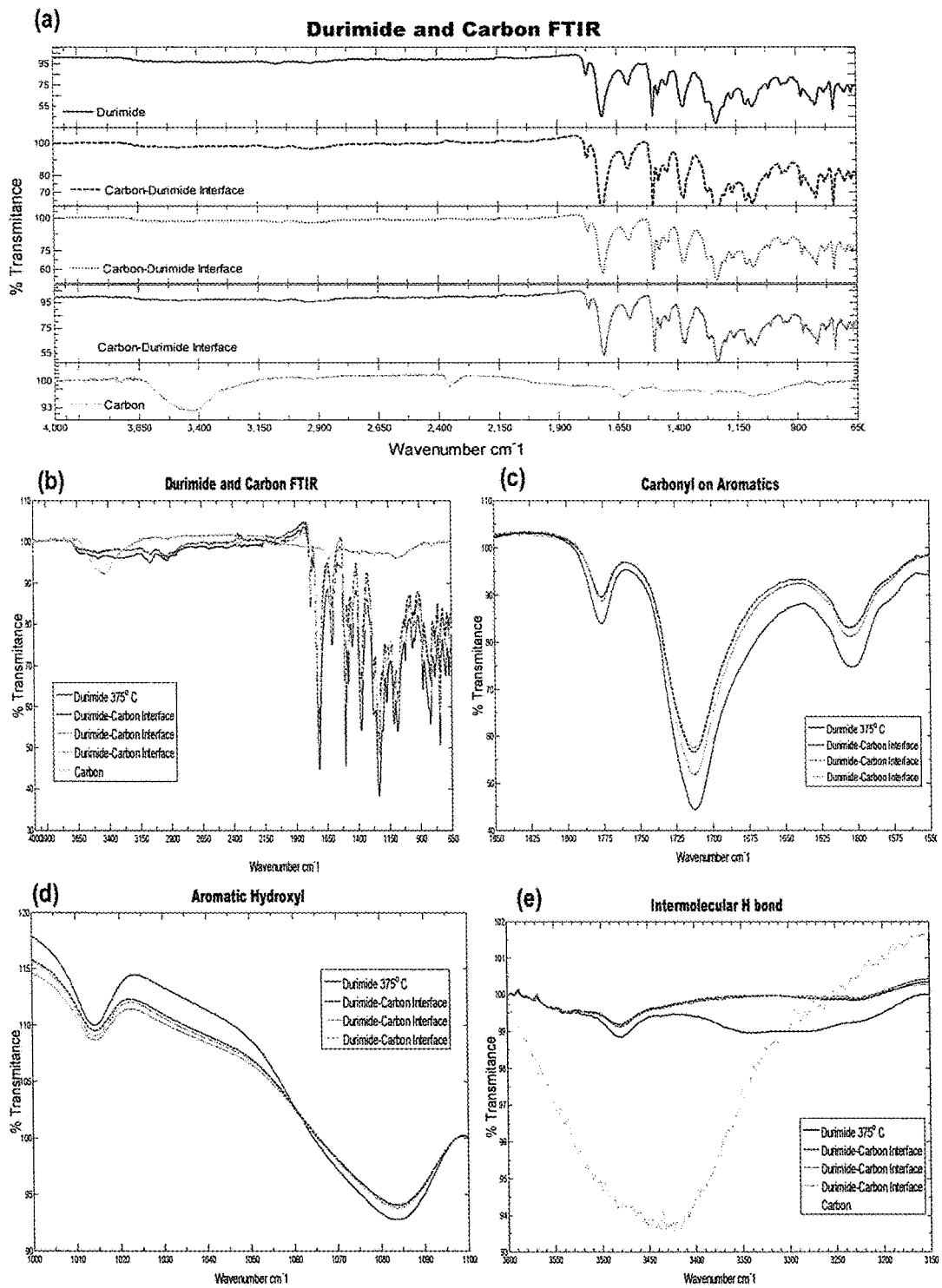
Figure 22. (a and b) FTIR spectra of polyimide, glassy carbon, and polyimide with glassy carbon showing c) shrinking of peaks corresponding to carboxyl group (d) broadening of the hydroxyl, (e) spectral changes indicating changes in the type of hydrogen bonding.

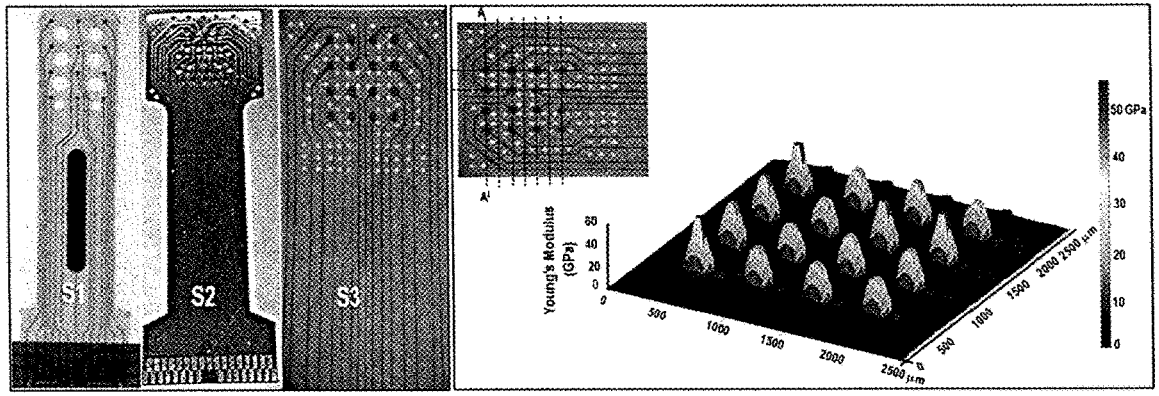

Figure 23 shows (a) Details of the three neural probes tested here. (b) Mapping of modulus of hybrid glassy carbon and polyimide microstructure (S3) with 4x4 array of microelectrodes using nanoindenter. Measurements were made at 10 points along a typical cross-section (e.g., A-A') covering both electrodes and polyimide substrate.

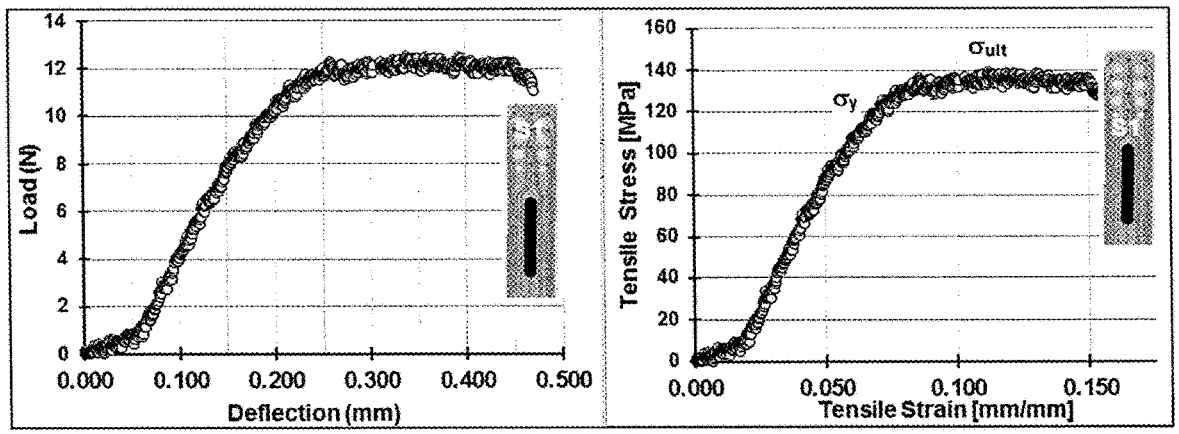

Figure 24. (a) Load-deflection curve (b) stress-strain curve for the test electrode set sample S1. The yield stress ($\sigma_y$) is ~18 MPa while ultimate stress ($\sigma_{ult}$) is ~20.9 MPa. The ultimate strain > 0.04%.

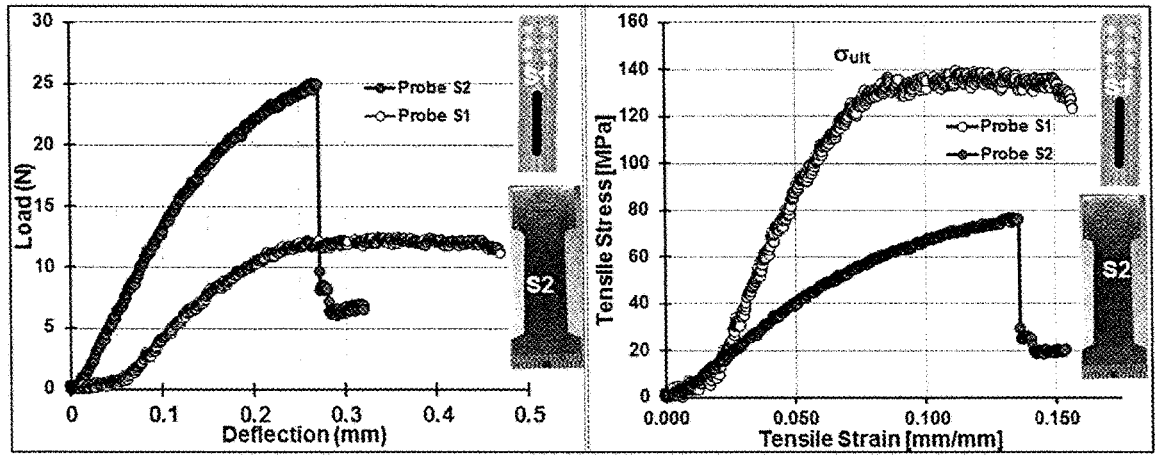

Figure 25. (a) Load-deflection curve (b) stress-strain curve for two electrode sets fabricated under different conditions demonstrating influence of fabrication on load carrying capacity and modulus.

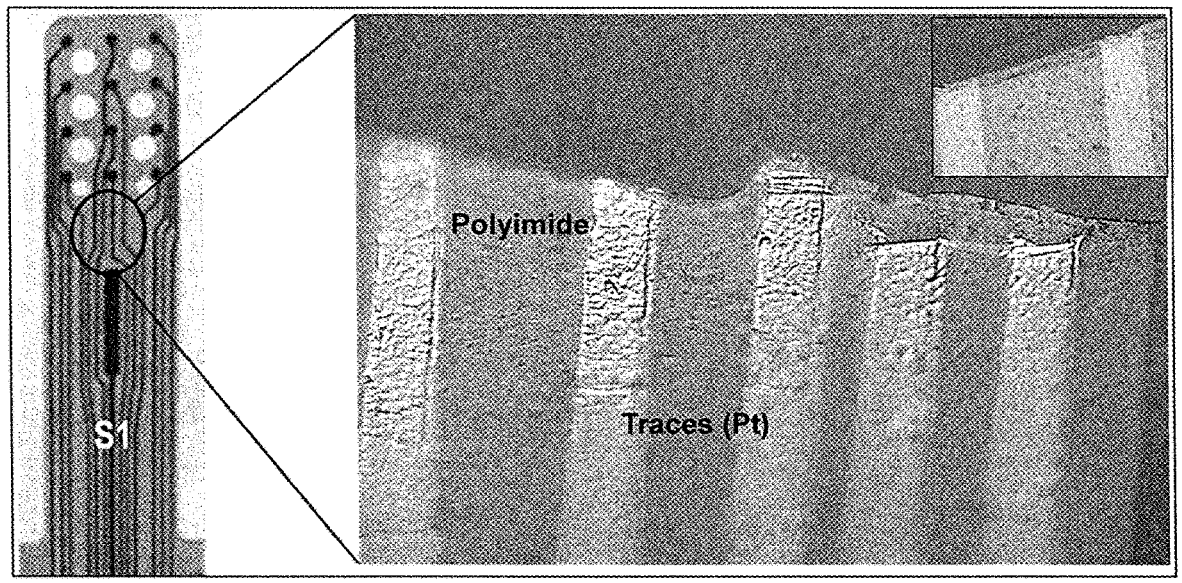

Figure 26. Electrode set S1 after failure during tensile test. The figure shows that the traces and polyimide layer held together as a unit indicating a strong bond between the two. The inset demonstrates that the traces are completely embedded in the polyimide layer.

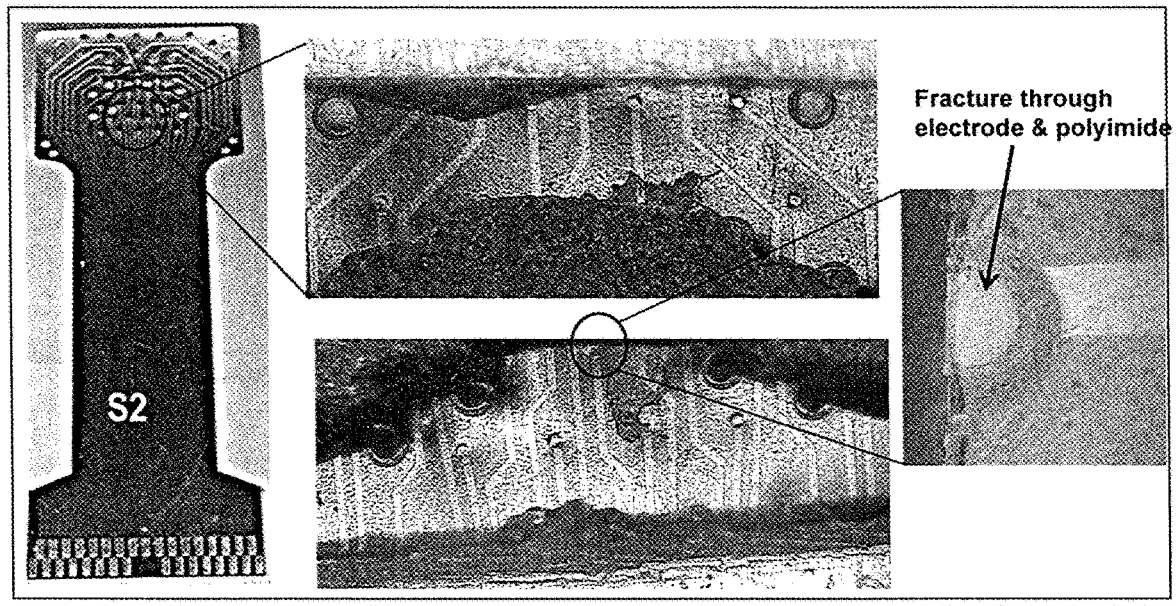

Figure 27. Electrode set S2 after failure during tensile test. Note the failure of the electrode/polyimide interface in the in-set demonstrating the rather strong bond between glassy carbon and polyimide. The fracture plane passes through not only the polyimide layer; but also through the electrode and splitting it into two pieces. This is an important finding that supports a good mechanical performance on this hybrid structure.

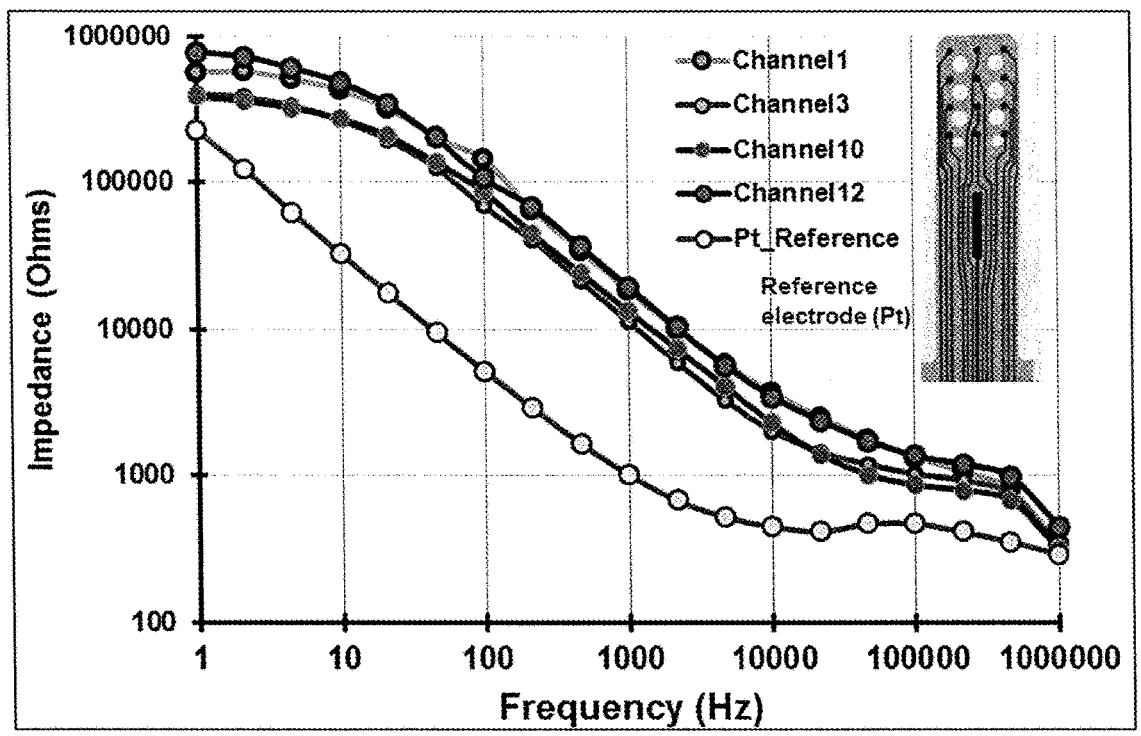

Figure 28. Impedance diagram for different channels of electrode set. The S1 electrode sets have electrodes of 300 μm dia, and 90 μm wide traces.

HYBRID METAL AND CARBON OR GLASSY CARBON MEMS µ-ECOG ELECTRODE AND MICROELECTRODE STRUCTURES

This United States Utility patent application claims priority to U.S. Provisional Application Ser. No. 62/051,295 filed on Sep. 16, 2014 and entitled "Electrical Impedance, Electrochemistry, Mechanical Stiffness, and Hardness Tunability in Glassy Carbon MEMS µ-ECOG Electrodes Structures" and U.S. Provisional Application Ser. No. 62/093,787 filed on Dec. 18, 2014 and entitled "Hybrid Metal and Glassy Carbon MEMS Microelectrodes for µ-ECOG System on Flexible Substrate", both of which are commonly-owned and incorporated in their entirety by reference.

STATEMENT REGARDING FEDERALLY SPONSORED RESEARCH

The invention was made with government support by National Science Foundation Grant Number EEC-1028725 under the Engineering Research Center or "ERC" program.

BACKGROUND

There is an increasing research interest in interfacing microelectrodes with tissues for applications ranging from neural signal sensing and stimulation in BCI (brain-computer interface) for sensorimotor control to chronic pain management, and deep brain stimulation (DBS), among others. In the specific area of neural probes, for example, substantial amount of research effort over the past several years had concentrated in advances in single and array of neural electrodes capable of recording signals from the brain as well as stimulating specific brain regions. These research efforts vary from those concentrating on stimulation and recording from a single neuron to complex networks of neurons using multiple electrodes in cortical and sensory areas in brains. For such probes, not only the architectures of the electrode structures, but also material properties are of major importance. Predictably, therefore, conventional and well-known materials that exhibit biocompatibility have been the traditional materials of choice. For instance, initial effort in neural probes employed glass tubes filled with electrolytes, where the glass acted as a biocompatible insulator. Later developments involved single and arrayed metal wire electrodes that were manually assembled in an array format.

MEMS (MicroElectroMechanical Systems) technology is interesting, because microfabrication of micron-sized electrodes arrays of variety of shapes using silicon, metal, and insulating and substrate materials, such as polyimide, have been made possible, thus spawning newer generation of neural electrodes. As a result, MEMS-based microelectrodes for neural recording and stimulation have, in general, enabled miniaturized and low-power high-density multisite arrays capable of interrogating a wider area. Carbon-based MEMS, which are fabricated by treating a pre-patterned organic structure made from negative tone photoresist polymer precursor to high temperatures in an inert or reducing environment, are finding applications in an increasing suite of devices such as fuel cells, plastic solar cells, bio-fuel cells, electrodes for dielectrophoretic cell separation systems, etc.

Carbon is finding increasing interest in the micro- and nanofabrication research community as a material of choice, where its conductivity, electrochemical stability in ionic solutions, response to chemical treatments for surface property modifications, and biocompatibility make it an ideal choice for electrochemical applications. With the added research and clinical desires to interface electronics with the human body for neural sensing and stimulation purposes, carbon—as an engineering material—can address numerous human health conditions for the research and industrial communities.

One photoresist that is commonly used in carbon-based and glassy carbon-based MEMS is SU-8, which is a high transparency, epoxy-based negative photoresist that enables creation of high-aspect-ratio structures using traditional UV photolithography. It derives its name from the presence of eight epoxy groups. The main advantages offered by glassy carbon material are excellent electrochemical stability, good electrical conductivity (low impedance), and excellent response to chemical surface treatments for surface property modifications. In addition, glassy carbon offers the ability to vary environmental conditions over a larger current-level, and hence pH, ionic concentration and temperature changes, making it an ideal choice for in-vivo bio-signal recording and stimulation. Moreover, patternable glassy carbon offers better and matched coupling with the tissues for use in bioelectronics due to its tailorable electrical, mechanical and electrochemical properties.

Because of the ease of manufacturing and structural flexibility that they offer, there has also been an increase in interest in polymer-based microelectrodes, particularly for ECoG (electrocorticography) applications, EEG (electroencephalography) applications and EMG (electromyography) applications. Tsang et al. had reported a flexible multisite microelectrode array of several electrodes for insect flight biasing using neural simulation. Rubehn et al. reported a 252-channel epicortical ECoG electrode array made of platinum electrodes on polyimide foil substrate. Their array had independently addressable electrodes and is among the largest electrode array reported so far. A stretchable electrode array for non-invasive wearable applications was developed by Ma et al. who used PDMS (poly dimethylsiloxane) substrate along with metal electrodes. However, their array was limited to EMG (electromyography) and EEG (electroencephalography) with no reported application in neural probing at the cortex or brain.

For µECoG or microelectrocorticographical applications, electrode materials that possess long-term high-fidelity performance in recording electrical and electrochemical signals are sought. As implanted devices, electrodes face a dynamically changing harsh biological environment where pH and ionic concentration fluctuate, and physical arrangement of blood vessels and neurons, for instance, shift. On the other hand, from tissue point of view, long-term implantable electrodes pose mechanical and electrochemical strains that affect the structure and health of cells of interest. Therefore, the minimization and elimination of these chronic detrimental interactions between electrodes and tissue is a major research focus. For this, the minimization of these mismatches by using a new class of electrode materials that are amenable to material property tailorability as well as lithographic patterning, such as glassy carbon (GC) is of significant research interest.

Glassy carbon, unlike almost all other microelectrodes, offers not only the unique electrical and electrochemical advantages of carbon, but also the ability to be patterned and also be mounted on substrates other than silicon, such as polyimide, which is stretchable and flexible. As a result, C-MEMS electrodes carry a significant potential to be a very competitive platform in complete sensor and actuator systems. This potential for a wider use of glassy carbon MEMS electrodes is, however, hampered by difficulties such as (i) incompatibility of their high-temperature pyrolysis process with CMOS, (ii) incompatibility of glassy carbon bump pads with soldering to metal wires, and (iii) thermal mismatch between resin and silicon substrate that produces warping of traces. Further, these electrodes have almost universally been fabricated on rigid silicon and quartz wafers—and hence severely limiting their wide applications—mainly because of the high-temperature process of pyrolysis that is integral to the fabrication.

However, as further progress in robust long-term clinical application of bio-probes is pursued, one of the fundamental challenges encountered in recording electrical and electrochemical signals from an implantable probe is their long-term high-fidelity performance. As implanted devices, electrodes face a dynamically changing harsh biological environment where pH and ionic concentration fluctuate, and physical arrangement of blood vessels and neurons, for instance, shift. On the other hand, from tissue point of view, long-term implantable electrodes pose mechanical and electrochemical strains that affect the structure and health of cells of interest. Therefore, the minimization and elimination of these chronic detrimental interactions between electrodes and tissue is a major research focus. For this, the major barriers that need to be overcome are the mismatch in mechanical stiffness, hardness, electrical impedance, and electrochemical behavior of the electrodes with that of tissue, which cause damages and risks associated with long-term tissue responses to implanted electrodes.

To enable long-term implantable devices, electrodes must be able to change mechanical stiffness, hardness, electrical impedance, and electrochemical behavior to match that of tissue. By creating glassy carbon-based MEMS electrodes and microstructures with tunable properties, devices suitable for micro-electrocorticography (ECoG) arrays can be manufactured that minimize the mismatches in properties that pose a barrier to biocompatibility of long-term implants. Therefore, it would be ideal to develop a class of electrode materials that are amenable to material property tailorability as well as lithographic patterning. In addition, it would be ideal if the materials have excellent conductivity, electrochemical stability in ionic solutions and excellent response to chemical surface treatments for surface property modifications, while at the same time being corrosion resistant, even in typical oxidizing environments. Attractive materials provide or allow an ability to tailor its mechanical, electrical, and electrochemical properties by varying the pyrolysis conditions, such as maximum temperature, duration of pyrolysis, and ramp rate. Ideal microstructures will have a fairly straightforward or easier manufacturing process. Ideal materials and microstructures would have at least some of the following applications: neural signal sensing, brain-computer interfacing, chronic pain management, deep brain simulation, fuel cells, solar cells, biofuel cells or a combination thereof.

SUMMARY OF THE SUBJECT MATTER

Microelectromechanical system are disclosed that include at least one electrode, microelectrode or combination thereof, wherein the at least one electrode, microelectrode or combination thereof comprises a carbon material, a glassy carbon material or a combination thereof. Contemplated systems are suitable for μ-ECoG arrays, EEG applications, EMG applications, along with other applications. In some embodiments, microelectromechanical system are disclosed that include at least one microstructure, sensor, actuator or combination thereof, wherein the at least one microstructure, sensor, actuator or combination thereof comprises a carbon material, a glassy carbon material or a combination thereof.

Another microelectromechanical system is disclosed that include at least one electrode, microelectrode or combination thereof, wherein the at least one electrode, microelectrode or combination thereof comprises a carbon material, a glassy carbon material or a combination thereof; at least one substrate, surface, layer or a combination thereof, wherein the at least one electrode, microelectrode or combination thereof is disposed on, coupled with or otherwise layered on the at least one substrate, surface, layer or a combination thereof. Yet another microelectromechanical system is disclosed that include at least one microstructure, sensor, actuator or combination thereof, wherein the at least one microstructure, sensor, actuator comprises a carbon material, a glassy carbon material or a combination thereof; at least one substrate, surface, layer or a combination thereof, wherein the at least one microstructure, sensor, actuator is disposed on, coupled with or otherwise layered on the at least one substrate, surface, layer or a combination thereof.

Additional microelectromechanical systems are disclosed that include at least one electrode, microelectrode or combination thereof, wherein the at least one electrode comprises a carbon material, a glassy carbon material or a combination thereof; at least one substrate, surface, layer or a combination thereof, wherein the at least one electrode, microelectrode or combination thereof is disposed on, coupled with or otherwise layered on the at least one substrate, surface, layer or a combination thereof; and at least one bump pad, wherein the at least one electrode, microelectrode or combination thereof is coupled with the at least one bump pad via at least one conductive metal. Yet additional microelectromechanical systems are disclosed that include at least one microstructure, sensor, actuator or combination thereof, wherein the at least one microstructure, sensor, actuator or combination thereof comprises a carbon material, a glassy carbon material or a combination thereof; at least one substrate, surface, layer or a combination thereof, wherein the at least one microstructure, sensor, actuator or combination thereof is disposed on, coupled with or otherwise layered on the at least one substrate, surface, layer or a combination thereof; and at least one bump pad, wherein the at least one microstructure, sensor, actuator or combination thereof is coupled with the at least one bump pad via at least one conductive metal.

A method of making a microelectromechanical system includes patterning a polymer precursor, a carbon-containing material or a combination thereof onto a surface, a substrate, at least one layer or a combination thereof; and heating or pyrolysing the polymer precursor, a carbon-containing material or a combination thereof in order to form a glassy carbon material.

Uses of microelectromechanical systems are also contemplated to measure at least one electrical property in a mammal or for electrocorticography.

BRIEF DESCRIPTION OF THE FIGURES

FIG. 1 shows: (a) Protocol for differing maximum pyrolysis temperatures and pyrolysis durations. For example, '600.2' and '1000.7' correspond to ramping rates of 4.8° C./min and 2.32° C./min respectively (b) negative photoresist (SU-8) is pyrolysed to glassy carbon pillars.

FIG. 2 shows: (a) Nano-indentation system for hardness and Young's Modulus test, (b) compliant z-stage with piezoelectric stack actuator, and (c) load-displacement curve.

FIG. 3 shows: (a) Young's Modulus for a variety of pyrolysis temperatures, (b) hardness of electrodes for a variety of pyrolysis temperatures.

FIG. 4 shows: (a) Impedance for a variety of pyrolysis temperatures of electrodes at 100 Hz, (b) Impedance vs frequency for a variety of pyrolysis temperatures for glassy carbon traces.

FIG. 5 shows: (a) Raman spectroscopy for a variety of pyrolysis temperatures at t=6 hours, (b) Raman spectroscopy for a variety of pyrolysis temperatures at t=7 hours.

FIG. 6 shows: (a) CIC for a variety of pyrolysis temperatures, (b) Transient of CIC after plasma treatment for a variety of pyrolysis temperatures (100 Watts for 60 Sec). Shows a temporary effect.

FIG. 7 shows: (a) Cyclic voltammetry measured and curve-fitting, (b) Equivalent Modified Randle circuit for the system. Rs=Solution Resistance, Rc=Charge Transfer Resistance (diameter of first semicircle), WS=Warburg Coefficient, CPE=Constant Phase Element at $\omega=1$.

FIG. 8 shows: (a) Alpha (multiplication factor of phase angle) vs pyrolysis temperatures, (b) charge transfer resistance (Rc) vs time of pyrolysis.

FIG. 9 shows: (a) Nyquist Plot for 6 hours of pyrolysis (b) Nyquist Plot for 7 hours of pyrolysis.

FIG. 10 shows fitted Nyquist Plots for 700-1000° C. pyrolysis temperature.

FIG. 11 shows a fabrication procedure for metal-CMEMS glassy carbon electrode.

FIG. 12 shows hybrid metal and glassy electrode probes. (a) SEM of glassy carbon electrodes after pyrolysis, (b) SEM of C-MEMS electrodes after pyrolysis and laying insulation layer, (c) bright-field microscope image of final microelectrode array, (d) front and back images of microelectrodes.

FIG. 13 shows details of a hybrid metal and glassy electrode probes. (a) SU-8 microelectrode before pyrolysis, (b) microelectrode structure after pyrolysis, (c) complete μECoG device with carbon electrodes connected to Hirose 40-pin connector, and glued to PCB for stability.

FIG. 14 shows mapping of Young's Modulus of Hybrid microelectrode array.

FIG. 15 shows: (a) Location of implantation of both Au/Pt and Au/C μECoG devices at motor cortex of rat model, (b) Electrode map and locations of elicited movements in anesthetized rat model.

FIG. 16 shows beta activity (main) and power spectra (top right) recorded by gold μECoG on anesthetized rat.

FIG. 17 shows beta activity (main) and power spectra (top right) recorded by carbon μECoG on anesthetized rat.

FIG. 18 shows lithography and pyrolysis process for fabricating glassy carbon electrodes from a negative tone photoresist. Silicon substrate with oxide layer is used. HF etches $SiO_2$ to release the final structure. The thickness of polyimide substrate is about 20 μm. Polyimide is cured at 375° C. for 2 hours in N2 atmosphere.

FIG. 19 shows: (a) Cross-section of pattern transfer process. (b) Shape of the pyrolysed electrodes is trapezoidal in elevation (conical in 3D) due to uneven shrinking during high-temperature pyrolysis process where both height and diameter decrease significantly. The bottom side that is constrained through attachment to silicon substrate shrinks less as compared to unconstrained sides. (c) electrodes flush with polyimide layer.

FIG. 20 shows complete glassy carbon electrode-set fabricated using the pattern transfer method described here. These microelectrode sets shown here (S1) are used for mechanical and electrical characterizations. The traces could be made from glassy carbon or metal. The electrodes have a diameter of 300 μm whereas the traces are 90 μm wide.

FIG. 21 (a) Steel bracket sample holder with electrode set in preparation for tensile test, (b) location of clamp support for both geometries of probes tested. For S1, the area of interest is the upper middle part of the probe with traces and polyimide, whereas for S2, the area of interest consists of electrodes, traces and polyimide substrate.

FIG. 21c shows: (a) Interface between polymer substrate and glassy carbon electrodes in S1 electrode set. (b) top surface of electrodes show good attachment with polyimide, (c) close-up view of polyimide and glassy carbon electrode interface.

FIG. 22 shows raman spectroscopy of glassy carbon showing D and H peaks.

FIG. 23 shows: (a) Details of the three neural probes tested here. (b) Mapping of modulus of hybrid glassy carbon and polyimide microstructure (S3) with 4×4 array of microelectrodes using nanoindenter. Measurements were made at 10 points along a typical cross-section49Load-deflection curve (b) stress-strain curve for the test electrode set sample. The yield stress ($\sigma_y$) is ~18 MPa while ultimate stress ($\sigma_{ult}$) is ~20.9 MPa. The ultimate strain >0.04%.

FIG. 24 shows: (a) Load-deflection curve (b) stress-strain curve for the test electrode set sample S1.

FIG. 25 shows: (a) Load-deflection curve (b) stress-strain curve for two electrode sets fabricated under different conditions demonstrating influence of fabrication on load carrying capacity and modulus.

FIG. 26 shows and electrode set S1 after failure during tensile test. The figure shows that the traces and polyimide layer held together as a unit indicating a strong bond between the two. The inset demonstrates that the traces are completely embedded in the polyimide layer.

FIG. 27 shows electrode set S2 after failure during tensile test. Note the failure of the electrode/polyimide interface in the in-set demonstrating the rather strong bond between glassy carbon and polyimide. This is an important finding that supports a good mechanical performance on this hybrid structure.

FIG. 28 shows an impedance diagram for different channels of electrode set. The S1 electrode sets have electrodes of 300 μm diameter and 90 μm wide traces.

DETAILED DESCRIPTION

A new and contemplated class of electrode materials are disclosed herein that are amenable to material property tailorability as well as lithographic patterning, such as glassy carbon (GC), which is derived from the pyrolysis of negative-tone resist polymers. Contemplated microstructures, such as GC microstructures, sensors, actuators and electrodes, (henceforth referred to us C-MEMS) made from lithographically patterned pyrolysed carbon have excellent conductivity, electrochemical stability in ionic solutions and excellent response to chemical surface treatments for surface property modifications. In contemplated embodiments, the at least one electrode, microelectrode or combination thereof is disposed on, coupled with or otherwise layered on a substrate, a surface, at least one layer or a combination thereof.

Contemplated materials and microstructures would have at least some of the following applications: neural signal sensing, brain-computer interfacing, chronic pain management, deep brain simulation, fuel cells, solar cells, biofuel cells or a combination thereof. They are designed, in some embodiments, to measure at least one electrical property in a mammal, which may comprise measuring current, voltage or a combination thereof. In some instances, contemplated embodiments are utilized for electrocorticography.

Contemplated embodiments, such as C-MEMS, offer an ability to tailor their mechanical, electrical, and electrochemical properties by varying the pyrolysis conditions such as maximum temperature, duration of pyrolysis, and ramp rate. By utilizing these unique properties of contemplated embodiments, a microelectrode structures is introduced that is suitable for µ-ECoG arrays, EEG applications and EMG applications with: (i) tailorable mechanical stiffness and that is inherently softer than RIE (reactive ion etched) silicon shanks or metals, offering a much better stiffness-matching with tissues, (ii) tailorable hardness and that is inherently softer than RIE silicon or metals for a better hardness-matching with soft tissues, and (iii) tailorable electrical impedance characteristics for better impedance-matching with neurons and tissues.

In some contemplated embodiments, a hybrid architecture is disclosed and described in detail where (i) the electrodes are made of patternable carbon or glassy carbon materials, whereas the traces and bump pads are microfabricated from metals, and (ii) the electrodes are mounted on a flexible substrate such as polyimide. This technology is demonstrated through the microfabrication of a novel biocompatible glassy carbon-based array of high aspect-ratio microelectrodes on a flexible substrate for applications in neural sensing and simulations, particularly for µ-ECoG systems.

Specifically, contemplated microelectromechanical system are disclosed that include at least one electrode, microelectrode or combination thereof, wherein the at least one electrode, microelectrode or combination thereof comprises a glassy carbon material. Contemplated systems are suitable for µ-ECoG arrays.

Another microelectromechanical system is disclosed that includes at least one electrode, microelectrode or combination thereof, wherein the at least one electrode, microelectrode or combination thereof comprises a glassy carbon material, at least one substrate, surface, layer or a combination thereof, wherein the at least one electrode, microelectrode or combination thereof is disposed on, coupled with or otherwise layered on the at least one substrate, surface, layer or a combination thereof.

Additional microelectromechanical systems are disclosed that include at least one electrode, microelectrode or combination thereof, wherein the at least one electrode, microelectrode or combination thereof comprises a glassy carbon material, at least one substrate, surface, layer or a combination thereof, wherein the at least one electrode, microelectrode or combination thereof is disposed on, coupled with or otherwise layered on the at least one substrate, surface, layer or a combination thereof; and at least one bump pad, wherein the at least one electrode, microelectrode or combination thereof is coupled with the at least one bump pad via at least one conductive metal.

A method of making a microelectromechanical system includes patterning a carbon-containing material onto a surface, a substrate, at least one layer or a combination thereof; and heating the carbon-containing material in order to form a glassy carbon material. Uses of microelectromechanical systems are also contemplated to measure at least one electrical property in a mammal or for electrocorticography.

This research reports on the mechanical, electrical, and electrochemical tunability of patternable glassy carbon microstructures fabricated through negative lithography and a pyrolysis process. The electrodes made from lithographically patterned glassy carbon have excellent electrochemical stability in ionic solutions and excellent response to chemical surface treatments for surface property modifications. The platform was demonstrated to have three useful tailorable properties: (i) tailorable mechanical stiffness that is softer than RIE silicon or metals offering a better stiffness-matching with the brain), (ii) tailorable electrical impedance characteristics for better impedance-matching with the brain, and (iii) tailorable electrochemical property useful for neurotransmitter electrochemical detections (variable reaction time).

The research showed that modulus, hardness, and electrochemical parameters (charge injection capacity, etc) not only increase with higher pyrolysis temperature; but also with higher ramp-rates (>8° C./min). Modulus and hardness values were observed to experience peak values at certain pyrolysis temperatures (800-900° C.), after which they seemed to decrease except for fast ramping-rates. Electrochemical parameters, on the other hand, seems to be negatively impacted only by slower ramping rates. It is suspected that the reasons could be structural changes in glassy carbon caused by the rearrangement of the ribbon-like carbon sheets with potential kinks and discontinuities in a given direction, and/or coalescing of pores caused by escaping of trapped hydrogen and other gases at even higher temperatures and lower ramping-rates where heat is applied over a longer period of time. The interplay between the different characteristics influenced by pyrolysis conditions was also investigated and concluded that, in general, ramping to the maximum pyrolysis temperature in 2 hours (ramp rate of 8.1° C./min) offers a more consistent protocol that results in C-MEMS with the optimized level of mechanical, electrical, and electrochemical behaviors that closely match those of soft-tissues.

It has been demonstrated and shown herein that glassy carbon or GC electrodes could have higher electro-kinetics at their surface with high charge injection capacity as compared to conventional metal probes, low impedance, and modulus in the range of 25-55 GPa. Therefore, these results can make C-MEMS microelectrodes the probes of choice for bio-signal sensing and stimulation applications, particularly for µ-ECoG systems.

A contemplated apparatus or system includes at least one electrode, and in some embodiments, a pair of electrode disposed on a substrate, surface, layer or combination thereof, wherein the electrodes comprise a glassy carbon, and wherein each of the electrodes comprise at least one microscale dimension, either collectively or individually, of less than about 1000 microns, less than about 500 microns, less than about 100 microns, less than about 25 microns, or less than about 10 microns is disclosed. It should be understood that the at least one microscale dimension and/or the at least one dimension comprises a length, a height, a depth and a width or a combination thereof, as outlined above.

Also disclosed is a method of making the apparatus, the method including (i) patterning a carbon-containing material, such as SU-8, on a substrate and (ii) heating the carbon-containing material, typically under conditions of less than 5% of oxygen or less than 1% oxygen, to form a glassy carbon material.

In other contemplated embodiments that comprise at least one bump pad via at least one conductive metal, an important consideration is the integrity of the connection between the glassy carbon electrodes, metal traces, and more importantly the insulating substrate or surface, such as a polyimide substrate. Bright-field microscope and SEM images confirmed that there is complete trace connections after the devices were lifted off. In addition, an important consideration is that of mechanical strength of the μ-ECoG array in withstanding the tensile forces applied by 4-0 surgical sutures to an individual suture hole during implantation. Finite element model was built to determine the stresses and strains developed under a load of 0.4N that is typically applied during suture. The FEA model showed that the stresses are about 60 MPa, only about 25% of the tensile strength of polyimide (215 MPa). With regard to electrical characterization of the array, the in-vivo tests were critical in demonstrating stimulation of the afferent motor neurons in the spinal cord with sufficient current to produce a muscular contraction.

As disclosed herein, a contemplated and novel microelectrode structure comprising carbon or glassy carbon microelectrodes (C-MEMS) patterned using traditional MEMS processes coupled with traces and bump pads made of metals, and mounted on a flexible and stretchable polyimide substrate has been produced. This unique architecture combines the unique electrical and electrochemical properties of C-MEMS with metals and, with its flexible substrate mounting, offers a new platform for electrical sensing and actuating probes.

Some contemplated embodiments include an apparatus including at least one electrode disposed on a substrate, surface, layer or combination thereof, such as a flexible substrate (e.g., polymeric, such as a polyimide), wherein the electrode(s) include a glassy carbon, and wherein the electrodes are electrically coupled to one or bump pads via a conductive metal, wherein each of the electrodes comprise at least one microscale dimension, collectively or individually, of less than about 1000 microns, less than about 500 microns, less than about 100 microns, less than about 25 microns, or less than about 10 microns.

Contemplated MEMS systems or apparatus may be biocompatible in a mammal, such as a human. The apparatus may be used for measuring electrical properties, such a voltage or current, in a mammal—in electrocorticography, for example. Also disclosed is a method of producing a contemplated MEMS system that includes: (i) patterning a carbon-containing material, such as SU-8, on a substrate, such as a sacrificial substrate (e.g., silica); (ii) heating the carbon-containing material, typically under vacuum or a reducing atmosphere, to form a glassy carbon material; (iii) forming a layer, such as a flexible layer, on exposed regions of the substrate; (iv) forming a patterned conductive metal layer that is electrically coupled to the glassy carbon, wherein the patterned conductive layer may include bump pads electrically coupled to the glassy carbon; (v) forming a layer, for example the same or similar material applied on the glassy carbon in step (iii), on the metal layer and optionally exposed regions of the layer formed in step (ii), and wherein the optional bump pads may be exposed; and (vi) removing the substrate to expose at least a portion of the glassy carbon, for example by etching.

EXAMPLES

Example 1: Evaluating Tunability of Glassy Carbon Structures Methods/Materials

The platform used for evaluating the tunability of glassy carbon structures comprises, and in some instances consists of, microelectrode arrays of cylindrical pillars of final dimensions of 700 μm height and 700 μm diameter (the starting sizes for the polymer precursor is 1 mm height and 1 mm diameter; but pyrolysis process results in 30-35% shrinkage). These sizes were chosen because they offer convenient and practical dimensions for mechanical and electrical characterizations; even though for μ-ECoG systems, the heights will be smaller (<10 μm).

The microfabrication process of the desired features comprises, and in some instances consists of, the traditional negative lithography processes (with slight variations for the various grades of negative-tone photoresist) followed by pyrolysis. In general, the process starts with deposition of SU-8 negative tone resist shown in FIG. 1b (1010) (MicroChem, Boston, Mass.) followed by lithography for patterning the microelectrode array. Subsequent to lithography, pyrolysis is carried out in a closed ceramic tube-furnace (by Lindberg Division of Sola Basic Industries of Watertown, Wis.) in vacuum or a forming gas (95% $N_2$ and 5% $H_2$) atmosphere through gradual heating to the desired temperature followed by cooling to room temperature. The key pyrolysis parameters that affect the chemical, mechanical, electrical, and electrochemical property of the final glassy carbon structures (1020) are rate of heating, pressure level, amount of nitrogen flow, and type of substrate. Out of these, the following parameters were kept constant: (i) continuous nitrogen flow of at least 2 L/min, (ii) and partial vacuum.

The parameters that were varied to tune the mechanical, electrical, and electromechanical properties were, (i) the maximum temperature of pyrolysis, and (ii) the heating protocol that governed temperature ramping, specifically the rate of temperature-ramping to the maximum pyrolysis temperature ($T_{max}$). The maximum pyrolysis temperatures of 600° C., 700° C., 800° C., 900° C., and 1000° C. were reviewed, under ramping time of 2-8 hours to $T_{max}$. The corresponding heating protocols are illustrated in FIG. 1a. For example, for 1000° C. pyrolysis temperature, two protocols are shown. In the first protocol, a total of 5 hours were required, with ramping from room temperature—1000° C. done in 2.0 hrs. (ramping rate of 8.1° C./min), held at 1000° C. (1 hr.), ramp-down from 1000° C. room temperature (2 hrs). In subsequent discussions, this protocol will be referred to as '1000.2' indicating that the maximum pyrolysis temperature was 1000° C. and the time to reach that temperature was 2 hours. In the second protocol, a total of 10.5 hours were required with ramping from room temperature—1000° C. done in 7.0 hrs. (ramping rate of 2.3° C./min), held at 1000° C. (1 hr.), and then ramped-down from 1000° C. —room temperature (2 hrs.). In this paper, the pyrolysis conditions are discussed primarily as a function of the ramping time to the maximum pyrolysis temperature.

Subsequent to lithography and pyrolysis, the pillars were kept in humidity and temperature-controlled environment (acrylic chamber under $1\times10^{-6}$ Torr vacuum and maintained at room temperature) and then subjected to mechanical, electrical, and electrochemical characterizations.

Results and Discussions

The material properties of glassy electrode microelectrode structures (pillars) pyrolysed under different temperatures were investigated, and the influence of the key pyrolysis parameters on the mechanical, electrical, and electrochemical properties of the final glassy carbon pillar-shaped microelectrode structures was evaluated. The interplay between the different physical properties of these structures as affected by the pyrolysis conditions such as maximum temperature, duration of pyrolysis, and ramp rate was also reviewed and discussed herein.

Electrode Characterization

The characterizations consisted of measuring mechanical properties (namely Young's Modulus and hardness), electrical impedance, electrochemical reactivity, and determining crystalline structure. These are described in detail below.

Mechanical Characterization

The mechanical properties (modulus and hardness) were measured using nanoindentation system for hardness and Young's Modulus test (210) shown in FIG. 2 that comprises (i) flexure based XY-stage for positioning specimen and (ii) flexure-based linear motion stage (Z-axis stage) that provides vertical positioning of the tool tip in addition to measuring the contact load of the tool. The vertical positioning mechanism comprises two independently moving stages; a reference frame for positioning of the tool, and mounting frame. This relative displacement between the two portions was used to determine the contact load acting on the tool. The Z-stage was actuated by PZT (lead zirconate titanate) piezoelectric stack actuator (220) (Tokin model AE0505D16F) driven by a piezoelectic power amplifier (AVL Instruments model 760), while the positions of the two independently moving portions of the Z-stage were determined through capacitance displacement sensors (Lion Precision driver model CPL 290 with probe model C3). The overall system was then controlled by software developed on a dSPACE platform (dSpace Inc., Wixom, Mich.).

Young's Modulus (E) and hardness (H) tests were performed on each pillar microelectrode structure at room temperatures using a 500 g load on the indenter. Load was applied until the indenter had stopped moving for at least 5 seconds. Calibrated microscope was used to measure the diamond-shaped indentation marks. Then, the modulus and hardness were calculated from the load-deflection relationship shown in FIG. 2c. The results on the variation of Young's Modulus and hardness are summarized in FIG. 3. The Young's Modulus seems to vary from a low of ~30 GPa to a maximum of 55 GPa. As expected, the GC pillars pyrolysed to only a maximum of 600° C. have the lowest values of modulus. However, for most ramping rates, except for 2 hours where there is no drop, the modulus values peak at 700-800° C. and then drop to values as low as 20 GPa. This is possibly caused by the coalescing of pores caused by escaping hydrogen and other gases. The Young's Modulus for un-pyrolysed negative resist (SU-8) was found to be 2 GPa and is similar to what is reported in the literature.

Electrical Characterization

The electrical characterizations consisted of AC impedance analysis by contacting each individual pillar microelectrode. AC impedance measurements were made using Solartron Analytical Model 1070E (manufactured by AMETEK Advanced Measurement Technology, Oakridge, Tenn.). This consisted of Galvanostatic impedance measurement in frequency range from 1 MHz to 1 Hz (frequency sweep) and amplitude of 3 mA. The results on impedance modulation are summarized in FIG. 4, which clearly shows a decrease in impedance with pyrolysis temperature from a high of ~100 KΩ at 600° C. to impedances as low as 10Ω for pyrolysis temperature of 1000° C. The biggest drop in impedance seems to be between 600° C.—700° C. of maximum pyrolysis temperature. FIG. 4b shows impedance changes with pyrolysis temperature for glassy carbon traces (as opposed to pillars), demonstrating the same pattern of impedance dependency of temperature for a variety of geometries.

Raman Spectroscopy

Raman spectroscopy was done on C-MEMS pillar structures using Thermo Nicolet DXR Raman Microscope (manufactured by ThermoScientific, Inc of Waltham, Mass.). FIG. 5 shows a Raman Spectroscopy of glassy carbon at different pyrolysis temperatures. Both disorder-induced, amorphous band (D-band) and graphitic band (G-band), which are characteristics of carbon material, were found in all pyroyzed specimens. The D-band at 1350/cm is due to microcrystallite graphite while the G-band at 1575/cm corresponds to single graphitic crystal with bond stretching motion pairs of $sp^2$ carbon atoms. As can be seen from the figure, the crystalline structure is not well developed with equal D-band and G-band until a pyrolysis temperature of 800° C. and more.

Electrochemical Characterization

Extensive electrochemical characterization was done through electrochemical impedance spectroscopy (EIS) and voltage transient tests. A buffer of PBS solution (0.13M NaCl, 0.022M $NaH_2PO_4 \cdot H_2O$, 0.081M $Na_2HPO_4 \cdot 7H_2O$ at pH~7.3) was used. All in vitro measurements were made in a three-electrode cell using a large-area Pt counter electrode, Ag/AgCl reference electrode, and glassy carbon working electrode.

The glassy carbon pillars were tested in 2×2 array; the back of the pillars in the array was attached to a copper foil using conductive silver paste and insulated with PDMS (so that only the top of the pillars touched the PBS solution). Extensive sets of experiments were performed to determine CIC (charge injection capacity), a value (multiplication factor of phase angle), $I_{peak}$ (peak current), and Rc (charge transfer resistance). These parameters quantitatively determine the electro-kinetics at the surface of electrodes, which in turn governs the suitability pf these electrodes as neural signal reading and stimulating electrodes in μ-ECoG systems. Charge injection capacity (GIG), the amount of charge that can move from the electrode to the solution without causing an irreversible chemical reaction (for glassy carbon, water window is +1V/−1V), was measured through voltage transient test, with 1 ms wide rectangular, biphasic, symmetric current pulse. The results on charge transfer kinetics are summarized in FIG. 6-10.

FIG. 6 shows CIC for a variety of pyrolysis temperatures. CIC of 1 $mC/cm^2$ (obtained for 1000.6 and 1000.7 protocols) is substantially higher than those reported for conventional probe materials such as Pt (0.3 $mC/cm^2$) and $Ta_2O_5$ (0.5 $mC/cm^2$). The effect of plasma treatment (100 Watts for 60 Sec) on CIC, for a variety of pyrolysis temperatures is also summarized in FIG. 6b where it is shown that plasma etching increases CIC, at least for a short term. However, as shown in the figure, the effect of oxygen plasma etching was predominately temporary and—at best—increased CIC only for few hours; the reason being that carboxyl groups created by plasma etching oxidize quite easily in open atmosphere. Nonetheless, the surface roughness caused by plasma etching could account for the slight long-term increase in CIC that was observed; an increase of roughness increases the ability of the material to inject charges to the solution in the reversible range.

FIG. 7 shows Nyquist plot and least-square curve-fitted cyclic voltammetry along with an equivalent modified Randle circuit (710) for the system. The equivalent circuit comprises solution resistance (Rs), double layer resistance (Rc), Warburg coefficient (Ws), and a constant phase element (CPE). The constant phase element, CPE represents an imperfect capacitor that simulates the effects of the double layer interaction between the solution and the surface of the glassy carbon microelectrodes. The CPE impedance is characterized by the equation:

$$Z_{CPE} = \frac{1}{C*\omega^a} e^{-ai*\left(\frac{\pi}{2}\right)} \qquad \text{Eq (1)}$$

Where the constant phase is −π/2α, C is the capacitance, and the exponent a is always greater than 0 and less than 1. As can be seen from Equation (1), when α is 1, the element behaves like a perfect capacitor. When α is 0, the element behaves like a resistor. The impedance from the CPE ($Z_{CPE}$) correlates with the height of the Nyquist plots. This capacitance was found to decrease with an increase in pyrolysis temperature which is consistent with the increase of outer Helmholtz double-layer at the electrode/electrolyte interface.

FIG. 8a shows the dependency of a parameter on the maximum pyrolysis temperature. The α values, which are a measure of the surface roughness, vary in the range 0.8-1. A decrease of α indicates an increase of the RSA (Real Surface Area). As seen from the figure, increase in the maximum pyrolysis temperature leads to α corresponding increase in the surface roughness. However the small decrease in a is likely due to some increase in surface roughness when pyrolyzed at higher temperatures, and thus a drift from the ideal capacitive behavior. The porosity of the glassy carbon electrode can be altered and optimized by varying the pyrolysis time.

FIGS. 9-10 show measured Nyquist plots for different pyrolysis temperature and different ramping. The diameter of the high frequency semicircle represents the charge transfer resistance Rc. Increase in the maximum pyrolysis temperature causes a decrease in the charge transfer resistance and a reduction of the double layer impedance. This reduced capacitive impedance is consistent with the increase of outer Helmholtz double-layer at the electrode/electrolyte interface, and hence the increase in the charge injection capacity of the pyrolyzed carbon microelectrodes when pyrolysis is carried out at higher temperatures. The Warburg element considered in the curve-fitted Nyquist plots in FIGS. 9-10 simulates an imperfect capacitor with a semi-infinite diffusion layer and represents the amount of diffusion of ionic species at the surface of the electrode. This phenomenon is predominant at low frequencies and nearly disappears at high frequencies. In the Nyquist plot, this element contributes a line with a 45 degree slope in ideal conditions. However, capacitance between some of the pillars may change the effect of the Warburg element generating an additional large and distorted semicircle rather than the commonly seen Warburg line.

Effect of Geometry and Time

The tests were repeated for different geometries consisting of thin glassy carbon traces (4 μm) and shorter pillars (100 μm-400 μm) to account for process and geometry effects. The results show that, in general, the key mechanical, electrical, and electrochemical properties of glassy electrode show a similar qualitative trend. Further, it was observed that glassy carbon tends to experience a change in electrical and electrochemical behavior with time due to surface oxidation. This can be remedied by thermal treatment through further pyrolysis or through voltage excursions. Further investigation on the time-dependent behavior is continuing and will be reported in a separate report.

Discussion

The mechanism of tunability of C-MEMS electrodes is better understood by closely looking at the characteristics of the ensuing material as the patterned resists are pyrolyzed. The possible chemical structural shape of glassy carbon has been described as "ribbon-like geometry of entangled carbon sheets" through HR-TEM (high-resolution transmission microscopy) where it is suggested that glassy carbon contains $sp^2$-hybridized carbons with six-membered rings as well as five and seven membered rings [38]. The pyrolysis of polymer precursors at different maximum temperatures gives rise to glassy carbons with different packing of this 'entangled' and dispersed carbon sheets. Subsequently, therefore, the distribution and shape of these ensuing ribbons of carbon sheets is the key determinant of the electrical and mechanical properties of glassy carbon material. In addition, the key structural changes that happen in the carbonization stage of pyrolysis (500-1200° C.) where $H_2$ attached to C is cleaved off and removed, and aromatic networks become connected determine the material characteristics of the ensuing glassy carbon. Intuitively, therefore, it appears that a compact packing in well-defined direction could give rise to higher modulus. Also, a compact packing of conductive carbon sheets will result in lower impedance. These effects, then, support the observation that varying the pyrolysis temperature and ramping rates, give rise to different packing and distribution of ribbons of carbon sheets, thereby accounting for the tunability reported here.

In general, this research demonstrates that modulus and hardness seem to increase with maximum pyrolysis temperature and slow ramp rate for temperature range of 600-800° C. However, this trend is reversed at pyrolysis temperatures greater than 800° C. Interestingly, for the protocol where the maximum pyrolysis temperature was reached in 2 hours, the maximum modulus was obtained at 900° C. (i.e., 900.2) followed by a decline similar to the other longer ramping-period protocols. The hardness of the pillars corresponding to this protocol, however, did not show a decline with higher pyrolysis temperature; the maximum hardness of 7 GPa being at 1000° C. This rather, unexpected behavior of glassy carbon has also been reported by Lee et al who had observed maximum modulus at around 800° C. for SU-8 (2) pre-cursor. This trend of dropping modulus—with increased pyrolysis temperature—after a certain 'peak' temperature is indicative of structural changes in glassy carbon at higher temperatures. Contemplated reasons could be (i) rearrangement of the ribbon-like carbon sheets with potential kinks and discontinuities in a given direction, and/or (ii) coalescing of pores caused by escaping of trapped hydrogen and other gases at even higher temperatures.

AC impedance, on the other hand, seems to follow a monotonic decrease with increasing pyrolysis temperature for a variety of geometries. Along the same line, electrochemical characterizations show interesting and monotonically increasing trends where higher pyrolysis temperature clearly results in higher CIC, low charge transfer resistance, and increased faradaic reactions at the electrode/electrolyte interface, and hence faster electro-kinetics. However, increasing ramping from 2 hours to 6 and 7 hours (and hence decreasing the actual heating rate) seems to consistently decrease the parameters affecting the electro-kinetics of the C-MEMS electrodes. Again, the reason for this trend of dropping electro-kinetics parameters—with decreased pyrolysis ramping rate—after a certain 'peak' temperature may be indicative of structural changes in glassy carbon due to a re-arrangement of the packing of the ensuing ribbon-like carbon sheets as heating is applied over a longer period of time.

In addition to this characterization of C-MEMS in the above discussed areas of stiffness, electrical conductivity and electrochemistry, what is, an important aspect is the interplay between each parameter and an investigation on whether each of these parameters can be modified independent of each other. In general, the correlation between the mechanical, electrical, and electrochemical parameters seem linear, with exceptions observed in some temperature ranges as shown in Table 1, which summarizes pyrolysis temperature ranges for optimized mechanical, electrical, and electrochemical characteristics. Whereas, the optimum conditions for most of the parameters seem to be between 700° C.—1000° C., the modulus and hardness, however, peak at a moderately lower temperature range of 700° C.—800° C., for most pyrolysis ramping rates (with the exception of 2 hours). The impedance and Raman spectroscopy measurements seem to provide a more distinct and narrower range (600° C.—700° C.) on the transition from mainly resistive behavior to conductive regime. This is well-corroborated by the tightening of the difference between D-band and G-band of Raman spectroscopy at 700° C., where conductive regime starts. In general, therefore, it can be inferred that ramping to the maximum pyrolysis temperature in 2 hours offers a more consistent protocol that results in C-MEMS with the optimized level of mechanical, electrical, and electrochemical behaviors, as shown in Table 2.

With regard to properties of soft tissues where these electrodes will be implanted, a summary of the range of mechanical and electrical properties of relevant tissues such as the cortex and spinal cord is given in Table 3. The table also summarizes mechanical and electrical properties of some of the known neural probes reported in the literature. As the table shows, the Young's Modulus of the Utah and Michigan microarrays are about 6 orders of magnitude higher than those of the cortex. In typical cases, high mechanical stiffness of a probe could lead to glial scar, and neurons possibly migrating away from electrodes and releasing cytotoxic chemicals. Similarly, higher impedance often results in low signal-noise ratios, whereas lower impedance could cause tissue damage. However, the Young's Modulus, hardness, impedance, and electro-kinetic parameters for C-MEMS electrodes reported here, therefore, seem to be far superior in closely matching the behavior of cortex and spinal soft tissues, than most of these reported electrodes materials.

Example 2: Analysis of the Hybrid Contemplated Architecture of Glassy Carbon Materials and Metals Methods/Materials In this section, contemplated microfabrication steps for the hybrid electrode system are disclosed and discussed. The glassy carbon MEMS microelectrodes are fabricated using standard negative photolithographic techniques for silicon wafers followed by pyrolysis in a furnace. The metal traces and bump pads are patterned through metal lift-off process.

The microfabrication process is shown in FIG. 11. It starts with deposition of SU-8 negative tone resist (15 μm) on a silicon dioxide substrate (1110) (oxide thickness of 1 μm-2 μm) followed by lithography for patterning the microelectrode array (1120). Subsequent to lithography, pyrolysis (1130) is carried out in a closed ceramic tube-furnace (Lindberg Division of Sola Basic Industries of Watertown, Wis.) in vacuum or a forming gas (95% $N_2$ and 5% H2) atmosphere through gradual heating to about 1000° C. followed by cooling to room temperature. Key parameters such as rate of heating, pressure level, amount of nitrogen flow, and type of substrate were modified in the pyrolysis process to achieve microelectrodes with excellent conductivity (R<1 KO) and a strong bond between the substrate and the glassy carbon. In some embodiments, SU-8 structures were microfabricated on a silicon wafer with 1-2 μm dioxide coating, and heated under continuous nitrogen flow of at least 2 L/min. The corresponding heating protocol is: room temperature-700° C. (1.5 hrs), 700-900° C. (1.5 hrs), 900-1000° C. (1.5 hrs), 1000° C. (1.5 hrs), 1000-900° C. (1.5 hrs), 900-700° C. (1 hour), and 700° C.—room temperature (auto-off).

The pyrolysis process is followed by spin-coating the first layer of 12 μm thick polyimide (FUJIFilm Electronics Materials, Mesa, Ariz.) and patterning it (1140). The pattern contains vias, leaving parts of the glassy carbon electrodes uncovered to allow access for the following metal traces. The polyimide is then cured at 375° C. under a nitrogen

TABLE 1

Pyrolysis Temperature Ranges for optimized characteristics

|  | Impedance | Mod, E | Hardness, H | $G_{peak}/D_{peak}$ | CIC | α | Rc |
|---|---|---|---|---|---|---|---|
| Temperature Range (° C.) | 800-1000 | 700-900 | 800-1000 | 700-1000 | 1000 | 900-1000 | 1000 |
| Ramping time (Hrs) | 2-7 | 2-6 | 2-6 | 2-7 | 6-7 | 2-7 | 2-6 |

TABLE 2

Summary of Electrochemical Characteristics. 2 hours of ramping.

| $T_{Pyrolysis}$ (° C.) | Rc (Ω) | W | α | C (mF/cm²) |
|---|---|---|---|---|
| 600 | — | — | 1 | |
| 700 | 373 | 651 | 1 | 10.71 |
| 800 | 361 | 605 | 1 | 12.86 |
| 900 | 210 | 615 | 0.96 | 200 |
| 1000 | 83 | 725 | 0.88 | 271.4 |

TABLE 3

Summary of Electrical and Mechanical Properties of Tissues.

| Tissue | Impedance (Ω) | E | H (GPa) |
|---|---|---|---|
| Cortex | Impedance (@ 1 kHz) for intercortical recording-50 Ω to 1M Ω [35] | 0.5 KPa-1 KPa [42] | NA |
| Spinal | Impedance (@ 1 kHz) for spinal cord signal recording, 50 KΩ-150 KΩ | 1.5 MPa with Pia Mater 0.1 MPa with no Pia Mater [43] | NA |
| Utah Microarray | 100 KΩ-300 KΩ [44] | 160-170 GPa | 13 GPa |
| Michigan Microarray | ~100-400 KΩ [45] | 160-170 GPa | 13 GPa |
| Polyimide Electrodes | 6 KΩ | 3-4 GPa (only substrate) | 0.1 GPa |
| Payrlene C | 6 KΩ | 2.8-3 GPa (only substrate) | 0.26 GPa |
| Current Study | 10 Ω-100 KΩ (@ 1 kHz) | 20 GPa (electrodes) | 3-6 GPa | atmosphere for 2 hours, to remove any remaining solvent from the material and effectively increasing the strength of the final product. A negative photoresist (Futurrex, Inc., Franklin, N.J.) is spun and patterned to form a sacrificial layer for the metal traces and bump pads (1150). Before depositing the metal layers, a reactive ion etch (500 mTorr of 02 at 100 W for 1 min) is used for descumming purposes, as well as to micro-roughen the polyimide surface. An adhesion layer of chromium (20 nm) is sputtered, followed by a layer of 200 nm thick gold (evaporated) (1160). The negative photoresist sacrificial layer is then removed in acetone, leaving only the metal traces and bump pads.

Another reactive ion etch (500 mTorr of $O_2$ at 100 W for 1 min) is then used to clean and micro-roughen the polyimide/metal structures interface. The final insulation layer of polyimide is then spin-coated (1170), patterned and cured as before followed by oxygen plasma etching (2 mins, 220 W 1 Torr), to ensure that the remaining polyimide and solvent residue on the bump pads are completely removed (1180). The thin-film devices are released using buffered aqueous HF solution (BHF) and the device soaked in deionized water, cleaned and dried. Polyimide shrinks vertically by about 40%-50% during the curing process, leaving the final polyimide structures less than 20 μm thick. For comparison purposes during characterization, a similar microelectrode structure with metal (gold) electrodes was microfabricated. The process is essentially the same, except negative lithography and pyrolysis steps are replaced by a simple one-step metal deposition.

FIG. 12 shows the released hybrid metal and glassy carbon electrode probe structure. Further details on SEM images of the carbon electrodes after pyrolysis and bright-field microscope image of final microelectrode array is also shown. SEM allowed for very high resolution images of the electrodes in both the metal and the hybrid devices. As can be seen in FIG. 12, processing the metal devices left a slight crater in which the gold electrode tip resides. The reason for this was due to the aspect ratio mismatch between the metal (total of 240 nm), and the polyimide insulation layer (~10 micron). Also, since the insulation layer was fabricated on top of the trace and electrode layers, the metal lies lower than the insulation layer. This feature serves as a means to further isolate the individual electrodes.

Alternatively, in the metal-carbon hybrid devices, the electrode tip was either flush as shown in FIG. 12b, or slightly raised above the polyimide. This feature was attributed, again, to the fabrication processing steps. Since the electrodes were fabricated first, followed by the base (1210), trace (1220), and insulation layers (1230), the electrodes (1240) were flush against the silicon dioxide substrate, along with the base layer surrounding it. After the buffered hydrofluoric acid etch, these electrodes were in fact flush with the base layer, instead of slightly indented. The microelectrode structure was then connected to Hirose 40-pin connector, and glued to PCB for stability as shown in FIG. 13c.

Results and Discussions

The mechanical (modulus and hardness), electrical (wet and dry impedance), and electrochemical (charge injection capacity, Warburg impedance, charge transfer resistance) characteristics of the hybrid electrode structures was investigated. The results of in-vivo testing of the microelectrodes with beta activity recording of stimulation signals and their power spectra are also reported.

Electrode Characterization

The characterizations consisted of measuring mechanical properties (namely Young's Modulus and hardness), electrical impedance, electrochemical reactivity, and determining crystalline structure as well as in-vivo testing. These are described in detail below.

Mechanical Characterization

The mechanical properties (modulus and hardness) were measured using nanoindentation system shown earlier in FIG. 2 that comprises (i) flexure based XY-stage for positioning specimen and (ii) flexure-based linear motion stage (Z-axis stage) that provides vertical positioning of the tool tip in addition to measuring the contact load of the tool. The vertical positioning mechanism comprises two independently moving stages; a reference frame for positioning of the tool, and mounting frame. This relative displacement between the two portions was used to determine the contact load acting on the tool. The Z-stage was actuated by PZT (lead zirconate titanate) piezoelectric stack actuator (Tokin model AE0505D16F) driven by a piezoelectic power amplifier (AVL Instruments model 760), while the positions of the two independently moving portions of the Z-stage were determined through capacitance displacement sensors (Lion Precision driver model CPL 290 with probe model C3). The overall system was then controlled by software developed on a dSPACE platform (dSpace Inc., Wixom, Mich.).

Modulus and hardness were measured for both the electrodes as well as the substrate to give a complete picture of the net modulus and hardness of the electrode system. FIG. 14 shows a summarized mapping (1410) of the modulus of the μECoG array where the average modulus of the electrodes was measured to be 50 GPa while that of the polyimide substrate was 2.5 GPa. The mapping gives a comprehensive pictorial view of the modulus of the μECoG array that the cortical tissues experience during long-term implantation.

Electrical Characterization

The electrical characterization consisted of determining the I-V curve, impedance curve, as well as four-point probe measurement of resistance. AC impedance measurements were made using Solartron Analytical Model 1070E (manufactured by AMETEK Advanced Measurement Technology, Oakridge, Tenn.). This consisted of linear sweep voltammetry from −2 to 2 Volt at a scan rate of 100 mV/s and galvanostatic impedance measurement in frequency range from 1 MHz to 1 Hz and amplitude of 3 mA. For the four-point probe resistance measurement, current was applied via a pair of force connections (current leads). A voltage drop was then generated across the impedance of the electrode structure to be measured according to Ohm's law V=RI. This current also generated a voltage drop across the force wires. To avoid including the voltage drop in the measurement, a pair of sense connections (voltage leads) were placed adjacent to the target impedance.

Electrochemical Characterization

Electrochemical characterization was done through electrochemical impedance spectroscopy (EIS) and voltage transient tests. A buffer of PBS solution (0.13M NaCl, 0.022M $NaH_2PO_4.H_2O$, 0.081M $Na_2HPO_4.7H_2O$ at pH ~7.3) prepared in DI water was used. All experiments were carried out at room temperature with 16 (4×4) identical working electrodes of the same area (150 um in diameter). All in-vitro measurements were made in a three-electrode cell using a large-area Pt counter electrode, Ag/AgCl reference electrode, and glassy carbon working electrode.

In addition, extensive sets of experiments were performed to determine CIC (charge injection capacity), which is the amount of charge that can move from the electrode to the solution without causing an irreversible chemical reaction (for glassy carbon, water window is +1V/−1 V). This was measured through voltage transient test, with 1 ms wide rectangular, biphasic, symmetric current pulse. CIC is also defined as the amount of charge per unit gross surface area (GSA) delivered in the leading phase of a stimulation pulse. A consistent value of 0.5 mC/cm$^2$ of CIC was found for C-MEMS electrodes whereas the value corresponding to gold electrodes was 0.06 mC/cm$^2$, again qualitatively demonstrating higher electrokinetics in C-MEMS as compared to metals. CIC for other conventional probe materials such as Pt is 0.3 mC/cm$^2$ and 0.5 mC/cm$^2$ for Ta$_2$O$_5$.

Rat In-Vivo Stimulation and Recording (μECoG)

In vivo testing was done on an anesthetized rat (the "subject") using the μECoG system built here following approved IUB protocols. The μECoG array contained smaller contacts (200 μm diameter) and traces (100 μm×200 μm).

Metal Electrodes and Traces (Au/Au)

After an incision was made and a small part of the subject's skull was removed, the Dura mater on top of the brain was carefully cut and peeled away, exposing a 2 mm×4 mm window to the motor cortex of the brain (FIG. 15a). A flexible μECoG array with gold traces and gold electrodes was connected through a Hirose connector to a recording amplifier. The device was then inserted underneath the Dura, on top of the left hemisphere of the brain, in the region of the motor cortex. The electrode map (1510) and locations of elicited movements (1520) are shown in FIG. 15b. Since the subject was anesthetized, brain activity was fairly low, and the recorded signal was not highly modulated. Nonetheless, beta activity (power in the ~15-30 Hz band) was recorded as can be seen in FIG. 16. Oscillations in ECoG signals represent synchronization of cortical activity in a local area. Changes in beta band oscillations are related to motor activity. Stimulation results were also obtained where clear, isolated movements in the nose, whiskers, right forelimb, and right shoulder of the rat (1530) were elicited by stimuli between 400 μA and 700 μA delivered to different electrodes on the 16 electrode array (1510) (FIG. 15b). Selective stimulation of specific motor pathways is an important requirement for Bas designed to control overt movements.

C-MEMS Electrodes and Metal Traces (C-MEMS/Au Hybrid)

No additional incision or drilling was required since the subject was already prepared for implantation. The Au/Au metal device was decoupled from the electronics, and a C-MEMS/Au hybrid device was connected. The device was placed once again below the Dura, on the motor cortex of the brain. During stimulation the device was again capable of eliciting movements from the nose and whiskers, as well as the shoulder and forelimb, indicating the ability of selective stimulation of the devices. Beta bursts were recorded using the carbon electrodes as well, indicating continuing cortical synchronization (FIG. 8). Interestingly, the carbon arrays were able to provide higher signal power in this low frequency region than the gold arrays. The large signal to noise ratio in the beta activity recordings of both the gold and the gold-carbon hybrid devices here indicate good connections and low impedance, as well as a strong capability to record biological signals. The beta bursts (power in the ~15-30 Hz band) are typically thought of as a measure of cortical synchronization in an area. Larger and broader SNR was observed in the carbon arrays with a corresponding bump in the power spectra.

Example 3: Pattern Transfer Techniques for Mounting C-MEMS Microelectrode Structures on Polymeric Flexible Substrates A novel technology for transferring glassy carbon microstructures originally fabricated on a silicon wafer through a high-temperature process to a polymeric flexible substrate such as polyimide. While glassy carbon microstructures patterned using MEMS process (i.e., Carbon-MEMS or C-MEMS) are finding increasing use in a variety of applications, their widespread use, however, been hampered by difficulties such as the high-temperature pyrolysis process (≥900° C.), which limits selection of substrates. The new approach presented in this example addresses this issue by first carrying out the patterning and high-temperature pyrolysis of a negative tone photoresist polymer precursor on silicon substrate, coating it with a polymer layer that chemically bonds with glassy carbon, and then releasing the ensuing glassy carbon structure; hence, transferring the structures to a flexible substrate. This enables the fabrication of unique set of glassy carbon microstructures (such as microelectrodes) that can be used in applications that demand substrates that conform to the shape of the stimulated/actuated or sensed surface. Detailed characterization for mechanical (stiffness, hardness, and tensile strength) and electrical (impedance) properties are reported. This pattern transfer technology makes C-MEMS technology useful to a wider user-base will enable the field of C-MEMS move forward in newer and exciting directions.

Polyimide is used to demonstrate this technology because of its excellent chemical and mechanical durability and patternability through lithography. In a specific research area of interest where glassy carbon electrodes have a superior performance, such as neural probes, for example, this new method could enable the fabrication of a complete electrode system with electrodes, traces, and bump pads. This technology is demonstrated here through the microfabrication of a novel bio-compatible glassy carbon-based array of microelectrodes on a polyimide flexible substrate for applications in neural sensing and simulations, particularly for microelectrocorticography systems.

Materials and Methods

For demonstrating the technology through an application area of growing research interest, an example of a series of μECoG (electrocorticography) microelectrode arrays with traces and bump pads designed for neural signal recording and stimulation is used.

Briefly, the microfabrication process is summarized in FIG. 18. It starts with deposition of SU-8 negative tone resist (20 μm) on a silicon substrate (1810) (with 1-2 μm thick oxide) followed by lithography for patterning the microelectrode array (1820). Subsequent to lithography, pyrolysis (1830) is carried out in a closed ceramic tube-furnace (Lindberg Division of Sola Basic Industries of Watertown, Wis.) in vacuum or a forming gas (95% N$_2$ and 5% H$_2$) atmosphere through gradual heating to about 1000° C. followed by cooling to room temperature. Contemplated, and in some cases key, parameters such as rate of heating, pressure level, amount of nitrogen flow, and type of substrate were optimized in the pyrolysis process to achieve microelectrodes with excellent conductivity and a strong bond between the substrate and the glassy carbon. Best results were found when SU-8 structures were microfabricated on a silicon wafer with 1-2 μm oxide coating, and heated under continuous nitrogen flow of at least 2 L/min.

The heating protocol used is: room temperature-700° C. (90 mins), 700-900° C. (90 mins), 900-1000° C. (90 mins), 1000° C. (90 mins), 1000-900° C. (90 mins), 900-700° C. (60 mins), and 700° C. ramped down to room temperature (auto-off). The pyrolysis process is followed by spin-coating (1840) the first layer of 20 μm thick photosensitive polyimide (FUJIFilm Electronics Materials, Mesa, Ariz.) and patterning it. If needed, the pattern could contain vias for access for metal traces which can subsequently be patterned through lift-off process. The polyimide is then cured at 375° C. under a nitrogen atmosphere for 2 hours. The devices are released (1850) using buffered aqueous HF solution and then soaked in deionized water, cleaned and dried. Polyimide shrinks vertically by about 40%-50% during the curing process, leaving the final polyimide structures less than 10 μm thick (1860).

FIG. 19 shows the cross-section of the released glassy carbon electrode probe structure (1910). Further details on SEM images of the glassy carbon electrodes after pyrolysis and pattern transfer is also shown in the same figure (1920). In this study, the demonstration of the pattern transfer technique and subsequent characterization through fabrication of three separate neural probes structures with designation of S1, S2, and S3, where each probe differs in geometry and fabrication conditions is the focus. Probe S1 has 180 μm diameter (3×4) electrodes and 600 μm dia breathing holes, and total width of 3 mm. S2 has 180 μm diameter (32#) electrodes, 600 μm dia breathing holes, and total width of 10 mm while S3 has (4×4) electrodes with diameter of 250 mm, breathing holes of 600 μm dia, and total width of 15 mm. Breathing holes are provided for allowing vascular growth in in-vivo applications. FIG. 20 shows such an electrode-set as fabricated. A complete glassy carbon electrode-set fabricated using the pattern transfer method described here is shown in FIG. 20. These microelectrode sets (2010 and 2020) shown (S1) are used for mechanical and electrical characterizations. The traces (2030) could be made from glassy carbon or metal. The electrodes (2040) have a diameter of 300 μm whereas the traces (2030) are 90 μm wide.

Characterizations

In this section, the mechanical (modulus, hardness, and tensile strength) and electrical (impedance) characteristics of glassy carbon electrode structures mounted on flexible substrate is discussed.

Interface Between Polymer and CMEMS Electrodes

The success of this pattern transfer technique strongly depends on the bond between polyimide and glassy carbon, particularly for applications that involve long-term exposure to severe humidity, high-temperature, and chemically-active environments. The following series of experiments determine the strength and stability of this bond through a variety of mechanical, optical, and electrical tests.

Chemical Property of Polyimide

Polyimides are a class of thermally stable polymers that are often based on stiff aromatic backbones. Key properties of polyimide are thermoxidative stability, high mechanical strength, high modulus, excellent insulating properties, and superior chemical resistance. Polyimide, especially the BPDA/PPD type, is most often used as biomaterial and commercially available under the trademark of DuPont's PI2611. Various groups have proven its biocompatbility, low cytotoxicity and low hemolytic capacity, both for bulk materials and long-term implanted electrodes. Surface treatment of polyimide through plasma etching, for example, results in formation of carbon radicals due to carbonyl oxygen losses. These radicals can then react with each other or with similar radicals on plasma treated glassy carbon electrode surface. Such covalent bonding is highly desirable and establishes strong attachment between polyimide and glassy carbon.

Interface Between Polyimide and Glassy Carbon

The interface between polyimide and glassy carbon is investigated visually through SEM as well as Raman spectroscopy. Visual inspection of SEM images of FIG. 21 shows that the polyimide and glassy carbon electrodes form a homogeneous bond with no noticeable gaps. Further, FIG. 21c shows polyimide coating partially removed revealing a surface that seems to stick very well to glassy carbon surface. Raman spectroscopy is also performed to determine what sort of chemical bonds exist between glassy carbon and polyimide. FIG. 22 shows FTIR spectra of polyimide, glassy carbon, and polyimide with glassy carbon showing: (c) shrinking of peaks corresponding to carboxyl group (d) broadening of the hydroxyl, (e) spectral changes indicating changes in the type of hydrogen bonding.

Mechanical Characterization

The mechanical characterization of the microstructure consisted of determining the Young's Modulus and tensile strength through a nanoindentation system and Instron universal testing machine, respectively. All three probe types, i.e., S1, S2, and S3 are characterized and shown in FIG. 23.

Modulus Test

The mechanical properties (modulus and hardness) are measured using nanoindentation system that consist of (i) flexure based XY-stage for positioning specimen and (ii) flexure-based linear motion stage (Z-axis stage) that provides vertical positioning of the tool tip in addition to measuring the contact load of the tool. Modulus and hardness are measured for both the electrodes as well as the substrate of probe S3 across multiple cross-sections to give a complete picture of the net modulus and hardness of the electrode system. As shown in FIG. 23, the average modulus of glassy carbon electrodes is measured to be 20 GPa while that of the polyimide substrate was 2.5 GPa. These values correspond very well with what is reported in the literature for glassy carbon and polyimide. Further details are given in previous work.

Tensile Test

Instron 5982 Universal Testing System is used to measure the tensile strength of a series of electrode sets. This model is equipped with a 100 kN load cell and is capable of tensile, compressive, and shears tests at extremely low strain rates. The testing device itself is composed of a stiff frame with two supports that house the opposite facing jaws of the device. The bottom jaw is static and mounts directly to the frame whereas the upper jaw is affixed to the actuated cross-piece that moves in a vertical direction. Two types of electrode sets (i.e., S1 and S2, with differing geometry and baking conditions for polyimide) are tested. Once the electrode set is clamped to two aluminum supports at both ends as shown in FIG. 21, a displacement controlled load is applied at a rate of 1 mm/min until complete failure of the device is observed. Typical failures are complete rupture of the electrode set. The parameters recorded are load, deflection, tensile stress (MPa) and tensile strain (%).

The load-deflection and stress-strain diagrams for both probes S1 and S2 are given in FIGS. 24 and 25. The electrode sets behave elastically when strained up to 2% of their initial length. Beyond that, the probe yields and begins displaying plastic behavior before completely failing towards 3% elongation. Two electrode sets of type S1 were successfully tested and were able to withstand maximum tensile loading of 20.9 MPa 23.9 MPa and exhibit a Modulus of 1.5 GPa and 1.3 GPa respectively. The much lower value for slope at <0.0005 strain in 1 is attributed to slack induced by the clamping. This 1.5 GPa and 1.3 GPa represent the strength of the carbon traces together with that of the polyimide and form a composite material that can be likened to a fiber reinforced material. Normally a combination such as this would be expected to exhibit a higher modulus along the orientation of the "fibers" which in this case is indeed true. Nanoindentation results seem to corroborate showing 3 GPa as the Young's modulus. This drop of ~1.7 GPa when compared to the nanoindentation results demonstrates the importance of testing the final devices in multiple modes and suggests that the probes could have of different properties in different directions. In this case the chips are weaker to in plane forces especially shear and compression, while being strong to normal compressive forces. This is further supported by the images taken of the breakage point along the chips.

The optical microscopy images of the failed specimen indicating the rupture zones are shown in FIGS. 26 (S1) and 27 (S2). The images indicate that the glassy carbon electrodes, traces, and polyimide substrate continue to behave as an ideal composite unit till failure where fracture zones actually pass through all these components. The inset in FIG. 28 shows that the failure plane not only passes through the electrode, but also makes a clean cut underlining the fact that the polyimide and glassy carbon electrode acted as one unit. It is remarkable that the electrodes are not pulled out of the substrate; but remain affixed to it till tensile failure occurs. This is an important finding that demonstrates almost a perfect bond between polyimide and glassy carbon electrodes.

The initiation of failure mechanisms in the probes S1 and S2 also give substantial information regarding the strength of the bond between polyimide, traces and electrodes. In S1 probe, the failure is initiated along a plane that contains both traces and polyimide substrate suggesting that failure occurred as the tensile strength of the composite was exceeded. In S2 probe, however, the location of the test sample subjected to tensile test comprises not only electrodes, traces, and substrates; but also breathing holes. The failure in this probe is initiated at area of weakness which is the breathing holes. Once the breathing holes failed by tearing, the load capacity decreases and the composite structure is strained in a plastic deformation until a rupture plane that passes through traces, electrodes, and polyimide is formed.

Electrical Characterization Through Impedance Spectroscopy

Electrical characterizations consisted of AC impedance analysis using a buffer of PBS solution (0.13 M NaCl, 0.022 M $NaH_2PO_4.H_2O$, 0.081 M $NaH_2PO_4.7H_2O$ at pH of ~7.3). AC impedance measurements were made using Solartron Analytical Model 1070E (AMETEK, Oakridge, Tenn.). This consisted of Galvanostatic impedance measurement in frequency range from 1 MHz to 1 Hz (frequency sweep) and amplitude of 10 µA. Several channels of electrode set S1 were tested, along with an on-board reference electrode made of platinum. As shown in FIG. 28, the impedance at 100 Hz (the usual standard frequency for bio-specific applications) for glassy carbon electrodes is between 100 KΩ-250 KΩ, ideal for surface micro-electrocorticography measurements. The impedance of the platinum reference electrode is much lower because of its large area, which is almost 20 times that of the glassy carbon electrodes. As each of the electrodes are geometrically and process-wise identical, the small difference in readings between each of the channels (electrodes) is possibly caused by differences in impedance of connecting wires.

Discussion

A key consideration in this new C-MEMS/metal hybrid µECoG array was the integrity of the connection between the glassy carbon electrodes, metal traces, and more importantly the insulating polyimide substrate. Bright-field microscope and SEM images confirmed that there is excellent trace connections after the devices were lifted off. In addition, an important consideration is that of mechanical strength of the µECoG array in withstanding the tensile forces applied by 4-0 surgical sutures to an individual suture hole during implantation. Finite element model was built to determine the stresses and strains developed under a load of 0.4N that is typically applied during suture. The FEA model showed that the stresses are about 60 MPa, only about 25% of the tensile strength of polyimide (215 MPa). With regard to electrical characterization of the array, the in-vivo tests were critical in demonstrating stimulation of the afferent motor neurons in the spinal cord with sufficient current to produce a muscular contraction.

Thus, specific embodiments of carbon and glassy carbon MEMS electrodes, microstructures and microelectrodes, their methods of production and uses thereof have been disclosed. It should be apparent, however, to those skilled in the art that many more modifications besides those already described are possible without departing from the inventive concepts herein. The inventive subject matter, therefore, is not to be restricted except in the spirit of the disclosure herein. Moreover, in interpreting the specification, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

REFERENCES

The references listed herein are considered relevant to the subject matter disclosed. Some of these are directly cited and others provide state of the art. Each of the following references are incorporated herein by reference in their entireties.

1. Hochberg, L. R. & Donoghue, J. P. "*Sensors for brain-computer interfaces*", IEEE Eng Med Biol Mag 25, 32-38 (2006).
2. Wang, W., Collinger, J. L., Degenhart, A. D., Tyler-Kabara, E. G., Schwartz, A. B., Moran, D. W., Weber, D. J., Wodlinger, B., Vinjamuri, R. K., Ashmore, R. C., Kelly, J. W. & Boninger, M. L. "*An Electrocorticographic Brain Interface in an Individual with Tetraplegia*", PLoS One 8, e55344 (2013).
3. Carmena, J. M., Lebedev, M. A., Grist, R. E., O'Doherty, J. E., Santucci, D. M., Dimitrov, D., Patil, P. G., Henriquez, C. S. & Nicolelis, M. A. "*Learning to Control a Brain-Machine Interface for Reaching and Grasping by Primates*", PLoS Biol 1, E42 (2003).
4. Chapin, J. K., Moxon, K. A., Markowitz, R. S. & Nicolelis, M. A. "*Real-time Control of a Robot Arm using Simultaneously Recorded Neurons in the Motor Cortex*", Nat Neurosci 2, 664-670 (1999).
5. Moritz, C. T., Perlmutter, S. I. & Fetz, E. E. "*Direct Control of Paralysed Muscles by Cortical Neurons*", Nature 456, 639-642 (2008).
6. Taylor, D. M., Tillery, S. I. & Schwartz, A. B. "*Direct Cortical Control of 3D Neuroprosthetic Devices*", Science 296, 1829-1832 (2002).
7. Bucher, Volker, Michael Graf, Martin Stelzle, and Wilfred Nisch, "*Low-Impedance Thin-Film Polycrystalline Silicon Microelectrodes for Extracellular Stimulation and Recording*", Biosensors and Bioelectronics. 1999; 14:639-649.

8. Hoffer, J., Richard Stein, Morten Haugland, Thomas Sinkjaer, William Durfee, Andrew Schwartz, Gerald Loeb, and Carole Kantor, "Neural Signals for Command Control and Feedback in Functional Neuromuscular Stimulation: A Review", Journal of Rehabilitation Research and Development. 1996; 33(2):145-157.

9. Hubel, D. H.; Wiesel, T. N. editor. "Ferrier Lecture: Functional Architecture of Macaque Monkey Visual Cortex", Proc. R. Soc. Lond. B. 1977, 198, 1-59

10. McLaughlin, D.; Shapley, R.; Shelley, M.; Wielaard, D. J. 'A Neuronal Network Model of Macaque Primary Visual Cortex (V1): Orientation Selectivity and Dynamics in the Input Layer '4C Alpha", PNAS 2000, 97, 8087-8092.

11. Normann, R. A.; Warren, D. J.; Ammermuller, J.; Fernandez, E.; Guillory, S. 'High-resolution Spatio-temporal Mapping of Visual Pathways using Multi-electrode Arrays'. Vision Res. 2001, 41, 1261-75.

12. Nicolelis, M. A. L; Ribeiro, S. 'Multiellectrode Recordings: the next steps'. Curr. Opin. Neurobiol. 2002, 12, 602-606.

13. Hoffman, K. L.; McNaughton, B. L. 'Coordinated Reactivation of Distributed Memory Traces in Primate Neocortex'. Science 2002, 297, 2070-2073.

14. Gesteland, R. C.; Howland, B.; Lettvin, J. Y.; Pitts, W. H. 'Comments on Microelectrodes'. Proc. Inst. Radio Eng. 1959, 47, 1856-1862.

15. Robinson, D. A. 'The Electrical Properties of Metal Microelectrodes'. Proc. IEEE 1968, 56, 1065-1071.

16. Skrzypek, J.; Keller, E. 'Manufacture of Metal Microelectrodes with Scanning Electronmicroscope', IEEE Trans. Biomed. Eng. 1975, 22, 435-437.

17. Wise, K. D.; Angell, J. B.; Starr, A. 'An Integrated-circuit Approach to Extracellular Microelectrodes'. IEEE Trans. Biomed. Eng. 1970, BME-17, 238-247.

18. Wise, K. D.; Najafi, K. 'Microfabrication Techniques for Integrated Sensors and Microsystems' Science 1991, 254, 1335-1342. Sensors 2008, 86722

19. Banks, D.; Ewins, D. J.; Balachandran, W.; Richards, P. R. 'Microengineered Interfaces with the Nervous System'. IEEE Colloqu. Med. Appl. Microeng. 1996, 4, 1-4.

20. Urban, G. A., Prohaska, O, Olcaytug, F. BioMEMS, Springer: Chicago, US, 2006; Chapter 1 (Early BioMEMS Multi-Sensor Neuroprobes), pp. 1-13.

21. Tsang W M, Stone A L, Aldworth Z N, Hildebrand J G, Daniel T L, Akinwande A I, Voldman J, 'Flexible Split-ring Electrode for Insect Flight Biasing using Multisite Neural Stimulation', IEEE Trans Biomed Eng. 2010 July; 57(7):1757-64.

22. Rubehn, B., Bosman, C., Oostenveld, R., Fries, P., and Stieglit, T., 'A MEMS-based Flexible Multichannel ECoG-electrode Array', Journal of Neural Engineering Volume 6 Number 3, 2009.

23. Ma R, Kim D H, McCormick M, Coleman T, Rogers J., 'A Stretchable Electrode Array for Non-invasive, Skin-mounted Measurement of Electrocardiography (ECG), Electromyography (EMG) and Electroencephalography (EEG)', Conf Proc IEEE Eng Med Biol Soc. 2010; 2010:6405-8.

24. Henle C, Fischer J, Meier W, Rickert J, Schuettler M, Stieglitz T "A Flexible ECoG-Electrode with High Resolution for BRAINCON—a wireless Implantable System for Long-term Recording and Stimulation", 2011 Biomed Tech, Volume: 56.

25. A Mercanzini, K Cheung, D L Buhl, M Boers, A Maillard, P Colin, "Demonstration of Cortical Recording using Novel Flexible Polymer Neural Probes", Sensors and Actuators A: Physical 143 (1), 90-96

26. Nyberg, T., Shimada A., Torimitsu K., "Ion Conducting Polymer Microelectrodes for Interfacing with Neural Networks", J Neurosci Methods. 2007 Feb. 15; 160(1):16-25.

27. Marin, C., Fernandez, E., "Biocompatibility of Intercortical Microelectrodes: Current Status and Future Prospects", Frontiers in Neuroengineering, Vol. 3, 8, 2010.

28. Ward, M. P., Rajdev, P., Ellison, C., Irrazouki, P. P., "Toward a Comparison of Microelectrodes for Acute and Chronic Recordings", Brain Research, 1282, 183-200, 2009.

29. Ranganathan, S. McCreey, R., Majji, S. M., Madou, M. "Photoresist-derived Carbon for Microelectromechanical Systems and Electrochemical Applications", J Electrochem Soc, 147 (2000), pp. 277-282.

30. Wang, C., Taherabadi, L., Jia., and Madou, M. "A Novel Method for the Fabrication of High-Aspect Ratio C-MEMs Structures", J. of Microelectromechanical Systems, 14(2), 348, 2005.

31. Kassegne, S. K., Wondimu, B., Mazjoub, M., and Shin, J., "High-Efficiency Microarray of 3-D Carbon MEMS Electrodes for Pathogen Detection Systems," Proc. SPIE, Vol. 7266, 726615 (2008), San Diego, Calif.

32. Wang, C. Taherabadi, L, Jia, G, Kassegne, S. K., Zoval, J, and Madou M J, Carbon-MEMS Architectures for 3D Microbatteries, Proceedings of the SPIE, 2004, Vol. 5455, p:295-302.

33. Hirabayashi, M., Mehta, B, Vahidi, N, Khosla, A., and Kassegne, S. K., "Functionalization and Characterization of Pyrolyzed Polymer Based Carbon Microstructures for Bionanoelectronics Platforms", Journal of Micromechanics and Microengineering, 23 (11), 115001, 2013.

34. Schueller, O. J. A., Brittain, S. T., Marzolin, C., and Whiteside, G. M., "Fabrication and Characterization of Glassy Carbon MEMS", Chem. Mater. 1997, 9, 1399-1406.

35. Cogan, S. F., "Neural Stimulation and Recording Electrodes", Annu. Rev. Biomed. Eng, 2008, 10:275-309.

36. Larsen, S. T., Argyraki, A., Amato, L., Tanzi, S., Keller, S. S., Rozlosnik, N., Taboryski, R. J., "Pyrolyzed Photoresist Electrodes for Integration in Microfluidic Chips for Transmitter Detection from Biological Cells", ECS Electrochemistry Letters, Vol. 2, No. 5, 2013, p. B5-B7.

37. Takmakov, P., Zachek, M. K., Keithley, R. B., Walsh, P. L., Donley, C., McCarty, G. S., and Wightman, R. M., "Carbon Microelectrodes with a Renewable Surface", Anal. Chem. 2010, 82, 2020-2028.

38. Sharma, S., and Madou, M. J., "Micro and Nano Patterning of Carbon Electrodes for BioMEMS", Bioinspired, Biomimetic and Nanobiomaterials, Volume 1, Issue 4, pages 252-265, ISSN: 2045-9858, E-ISSN: 2045-9866, 2012.

39. Lee, J. A., Lee, S. W., Lee, K-C, L., Park, S I, "Fabrication and Characterization of Freestanding 3D Carbon Microstructures using Multi-Exposures and Resist Pyrolysis", Journal of Micromechanics and Microengineering, 18, 035012, 2008.

40. Rousche P. J., Normann R. A. (1992). "A Method for Pneumatically Inserting an Array of Penetrating Electrodes into Cortical Tissue". Ann. Biomed. Eng. 20, 413-422

41. Szarowski et al, "Brain Response to Micromachined Silicon Devices", Brain Research, 983, 2003.

42. Van Dommelen, J., et al "Mechanical Properties of Brain Tissue by Indentation", J. of. Mech. Beh. Of Biomedical Materials, 3, 2010.

43. Mazuchwski & Thebault, "*Biomechanical Properties of the Human Spinal Cord & Pia Mater*", Soft Matter, 3, 2007.
44. Maynard, E. M., Nordhausen, C. T., Normann, R. A., "*The Utah Intracortical Electrode Array: A recording structure for potential brain-computer interfaces*", Electroencephalography and Clinical Neurophysiology, Volume 102, Issue 3, March 1997, Pages 228-239.
45. Hoogerwerf, A. G. and Wise, K. D., "*A Three-Dimensional Microelectrode Array for Chronic Neural Recording*", IEEE Trans Biomed Eng. 1994 December; 41(12): 1136-46.
46. Wang, C., Madou, M., "*From MEMS to NEMS with carbon*", Short communication, Biosensors and Bioelectronics 20 (2005) 2181-2187.
47. J. Hammacher, A. Fuelle, J. Flaemig, J. Saupe, B. Loechel and J. Grimm, '*Stress engineering and mechanical properties of SU-8-layers for mechanical applications*'. Microsyst. Technol., 14 (2008), pp. 1515-1523.

We claim:

1. A microelectromechanical system, comprising:
   at least one microelectrode, wherein the at least one microelectrode comprises a glassy carbon material, wherein the glassy carbon material is made from lithographically-patterned pyrolysed carbon;
   at least one substrate, surface, layer or a combination thereof, wherein the at least one substrate, surface, layer or a combination thereof comprises a flexible polymeric substrate, and wherein the at least one microelectrode is disposed on, coupled with or otherwise layered on the at least one substrate, surface, layer or a combination thereof; and
   at least one bump pad, wherein the at least one microelectrode is coupled with the at least one bump pad via at least one conductive metal, wherein the microelectromechanical system is suitable for use in humans.

2. The microelectromechanical system of claim 1, wherein the system is biocompatible with a mammal.

3. The microelectromechanical system of claim 1, wherein the system is a sensor, an actuator or a combination thereof.

4. The microelectromechanical system of claim 1, wherein the at least one microelectrode comprises at least one dimension.

5. The microelectromechanical system of claim 4, wherein the at least one dimension comprises a length, a height, a depth, a width or a combination thereof.

6. The microelectromechanical system of claim 5, wherein the at least one dimension has an individual or combined length, height, depth, width or combination thereof of less than about 1000 microns.

7. The microelectromechanical system of claim 5, wherein the at least one dimension has an individual or combined length, height, depth, width or combination thereof of less than about 500 microns.

8. The microelectromechanical system of claim 5, wherein the at least one dimension has an individual or combined length, height, depth, width or combination thereof of less than about 100 microns.

9. The microelectromechanical system of claim 5, wherein the at least one dimension has an individual or combined length, height, depth, width or combination thereof of less than about 25 microns.

10. The microelectromechanical system of claim 5, wherein the at least one dimension has an individual or combined length, height, depth, width or combination thereof of less than about 10 microns.

11. The microelectromechanical system of claim 1, wherein the at least one microelectrode comprises at least one microscale dimension.

12. The microelectromechanical system of claim 11, wherein the at least one microscale dimension comprises a length, a height, a depth, a width or a combination thereof.

* * * * *